US009442092B2

(12) United States Patent
Lane

(10) Patent No.: US 9,442,092 B2
(45) Date of Patent: Sep. 13, 2016

(54) METHODS FOR TREATMENT OF AUTISM

(76) Inventor: Kerry Lane, West Palm Beach, FL (US)

(*) Notice: Subject to any disclaimer, the term of this patent is extended or adjusted under 35 U.S.C. 154(b) by 0 days.

(21) Appl. No.: 14/127,493

(22) PCT Filed: Jun. 19, 2012

(86) PCT No.: PCT/US2012/043161
§ 371 (c)(1),
(2), (4) Date: Dec. 19, 2013

(87) PCT Pub. No.: WO2012/177647
PCT Pub. Date: Dec. 27, 2012

(65) Prior Publication Data
US 2014/0112940 A1 Apr. 24, 2014

Related U.S. Application Data

(60) Provisional application No. 61/499,027, filed on Jun. 20, 2011.

(51) Int. Cl.
A61K 39/395 (2006.01)
G01N 33/53 (2006.01)
G01N 27/62 (2006.01)
A61B 5/00 (2006.01)
G01N 33/68 (2006.01)
A61B 5/1455 (2006.01)

(52) U.S. Cl.
CPC ............ G01N 27/62 (2013.01); A61B 5/1455 (2013.01); A61B 5/4076 (2013.01); G01N 33/6893 (2013.01); A61B 5/4082 (2013.01); A61B 5/4088 (2013.01); G01N 2333/37 (2013.01); G01N 2800/28 (2013.01); G01N 2800/368 (2013.01); G01N 2800/50 (2013.01)

(58) Field of Classification Search
None
See application file for complete search history.

(56) References Cited

U.S. PATENT DOCUMENTS

| | | |
|---|---|---|
| 4,126,701 A | 11/1978 | Taylor |
| 5,008,251 A | 4/1991 | Gruber |
| 5,225,407 A | 7/1993 | Oakley et al. |
| 5,527,825 A | 6/1996 | Karson et al. |
| 5,686,311 A | 11/1997 | Shaw |
| 5,837,729 A | 11/1998 | Bourinbaiar |
| 6,058,940 A | 5/2000 | Lane |
| 6,197,749 B1 | 3/2001 | Hamuro et al. |
| 6,270,953 B1 | 8/2001 | Malcus-Vocanson et al. |
| 6,362,226 B2 | 3/2002 | Phillips, III et al. |
| 6,470,894 B2 | 10/2002 | Hersch et al. |
| 6,512,166 B1 | 1/2003 | Harman et al. |
| 6,790,825 B2 | 9/2004 | Beck et al. |
| 6,899,876 B2 | 5/2005 | Houston |
| 7,232,575 B2 | 6/2007 | Walsh et al. |
| 7,252,957 B2 | 8/2007 | Vojdani |
| 7,378,387 B2 | 5/2008 | Hamuro et al. |
| 7,452,681 B2 | 11/2008 | Amaral et al. |
| 7,534,450 B2 | 5/2009 | Walsh et al. |
| 7,604,948 B2 | 10/2009 | Amaral et al. |
| 7,749,509 B2 | 7/2010 | Cobb et al. |
| 7,803,531 B2 | 9/2010 | Fulton et al. |
| 7,939,066 B2 | 5/2011 | Puntenney et al. |
| 7,981,878 B2 | 7/2011 | Hubmann et al. |
| 8,170,803 B2 | 5/2012 | Kamath et al. |
| 9,056,050 B2 | 6/2015 | Fallon et al. |
| 9,150,608 B2 | 10/2015 | Ip et al. |
| 2012/0141510 A1 | 6/2012 | Doronina et al. |
| 2012/0259017 A1 | 10/2012 | Nayak et al. |
| 2014/0221465 A1 | 8/2014 | Bancel et al. |
| 2015/0150862 A1 | 6/2015 | Hood et al. |
| 2015/0211039 A1 | 7/2015 | Wang et al. |
| 2015/0259341 A1 | 9/2015 | Ceccarelli et al. |

FOREIGN PATENT DOCUMENTS

WO WO 2008/124187 A1 10/2008
WO WO 2010/066000 A1 6/2010

OTHER PUBLICATIONS

Abstract for Menzel, Arthur E.O., et al; The Isolation of Gliotoxin and Fumigacin From Culture Filtrates of Aspergillus Fumigatus, The Journal of Biological Chemistry, Feb. 1, 1994; 152, p. 419-429.
PubMed Abstract for Kaur, P., et al.; Role of glutathione in determining the differential sensitivity between the cortical and cerebellar regions towards mercury-induced oxidative stress, Toxicology, vol. 230, Issues 2-3, Feb. 12, 2007, pp. 164-177.
PubMed Abstract for Kaur, P., et al.; Glutathione modulation influences methyl mercury induced neurotoxicity in primary cell cultures of neurons and astrocytes, Neurotoxicology, Jul. 2006; 27(4):492-500.
PubMed Abstract for Sutton, P., et al.; Exacerbation of invasive aspergillosis by the immunosuppressive fungal metabolite, Gliotoxin, Immunology and Cell Biology, Aug. 1996; 74(4),318-322.
PubMed Abstract for Osorio, J.C., et al.; Influence of maternal redox status on birth weight, Reprod. Toxicol, Jan. 2011; 31(1):35-40.

(Continued)

Primary Examiner — Olga N Chernyshev
(74) Attorney, Agent, or Firm — Karan Singh

(57) ABSTRACT

The current invention is directed towards a rapid, reproducible test for the fungal virulence factors and associated affected compounds so that patients at risk for autism, cerebral palsy and other human diseases can be quickly identified, treated and possibly prevented. This includes a multitude of test protocols for both the mycotoxin gliotoxin and its relationship with glutathione—and relates the two molecules by a novel paradigm known as the Glutathione-Gliotoxin Index—(GGI) or Disease-Disorder Susceptibility Index—D/DSI, which indicates the Autism Susceptibility Index—(ASI). One testing device and protocol includes a cellular phone application with modification to test for susceptibility to autism and other disease states. Of particular relevance for autism is the role of glutathione depletion by gliotoxin, then by the anti-pyretic acetaminophen in the peri-vaccination period, which each result in oxidative stress and metal intoxication, by disrupting the metallothionein system, amongst other biochemical pathways and numerous enzyme systems.

20 Claims, No Drawings

(56) References Cited

OTHER PUBLICATIONS

PubMed Abstract for Mistry, H.D., et al.; The importance of antioxidant micronutrients in pregnancy, Oxid Med Cell Devel., Sep. 13, 2011; 2011:841749.

PubMed Abstract for Knapen, M.F., et al.; Low whole blood glutathione levels in pregnancies complicated by preeclampsia or the hemolysis, elevated liver enzymes, low platelets syndrome, Obstet Gynecol, Dec. 1998; 92(6):1012-5.

PubMed Abstract for Spickett, C.M., et al.; Erythrocyte glutathione balance and membrane stability during preeclampsia, Free Radic Biol Med., Apr. 1998; 24(6):1049-55.

PubMed Abstract for Knapen, M.F., et al.; Plasma glutathione S-transferase alpha 1-1: a more sensitive marker for hepatocellular damage than serum alanine aminotransferase in hypertensive disorders of pregnancy, AM J Obstet Gynecol, Jan. 1998; 178(1 Pt 1):161-5.

PubMed Abstract for Zhao, Z., et al.; Reduced glutathione prevents nitric oxide-induced apoptosis in vascular smooth muscle cells, Biochim Biophys Acta., Nov. 27, 1997; 1359(2):143-52.

PubMed Abstract for Yang, Y., et al.; Glutathione-S-transferase A4-4 modulates oxidative stress in endothelium: possible role in human atherosclerosis, Atherosclerosis, Apr. 2004;173(2):211-21.

PubMed Abstract for Sharma, R., et al.; Antioxidant role of glutathione S-transferases: protection against oxidant toxicity and regulation of stress-mediated apoptosis, Antioxid Redox Signal, Apr. 2004; 6(2):289-300.

PubMed Abstract for Lane, K.S., Aflatoxin, Tobacco, Ammonia and the p53 Tumor-Suppressor Gene: Cancer's Missing Link?, Med Gen Med, Aug. 30, 1999:E10.

PubMed Abstract for Perron, H., [MSRV retrovirus and gliotoxin protein: potential biological markers in multiple sclerosis?] [Article in French] , Ann Biol Clin (Paris), Jul.-Aug. 1998; 56(4):427-38.

PubMed Abstract for Sutariya, V., et al.; Development and validation of a novel RP-HPLC method for the analysis of reduced glutathione, J Chromatogr Sci, Mar. 2012; 50(3):271-6.

PubMed Abstract for Khan, A., et al.; Simultaneous determination of cefdinir and cefixime in human plasma by RP-HPLC/UV detection method: Method development, optimization, validation, and its application to a pharmacokinetic study, J Chromatogr B Analyt Technol Biomed Life Sci., Aug. 15, 2011; 879(24):2423-9.

PubMed Abstract for Brittain, H.G., Applications of chiroptical spectroscopy for the characterization of pharmaceutical compounds, J Pharm Biomed Anal, Sep. 1, 1998; 17(6-7):933-40.

PubMed Abstract for Schutze, N., et al.; Exposure to mycotoxins increases the allergic immune response in a murine asthma model, Am J Respir Crit Care Med, Jun. 1, 2010; 181(11):1188-99.

PubMed Abstract for Empting, L.D., Neurologic and neuropsychiatric syndrome features of mold and mycotoxin exposure, Toxicol Ind Health, Oct.-Nov. 2009; 25 (9-10):577-81.

PubMed Abstract for Peterson, J.D., et al.; Glutathione levels in antigen-presenting cells modulate Th1 versus Th2 response patterns, Proc Natl Acad Sci USA, Mar. 17, 1998; vol. 95 No. 6., 3071-3076.

PubMed Abstract for Comera, C., et al.; Gliotoxin from Aspergillus fumigatus affects phagocytosis and the organization of the actin cytoskeleton by distinct signaling pathways in human neutrophils, Microbes Infect., Jan. 2007; 9(1):47-54.

PubMed Abstract for Shah, D.T., et al.; In situ mycotoxin production by Candida albicans in women with vaginitis, Gynecol Obstet Invest., 1995; 39(1):67-9.

PubMed Abstract for Aukrust, P., et al.; Disturbed Glutathione Metabolism and Decreased Antioxidant Levels in Human Immunodeficiency Virus-Infected Patients during Highly Active Antiretroviral Therapy—Potential Immunomodulatory Effects of Antioxidants, J Infect Dis., Jul. 15, 2003; 188 (2): 232-238.

PubMed Abstract for Bishop, C., et al.; A Pilot Study of the Effect of Inhaled Buffered Reduced Glutathione on the Clinical Status of Patients With Cystic Fibrosis, CHEST, Jan. 2005; vol. 127 No. 1, 308-317.

PubMed Abstract for Grimble, R.F., The Effects of Sulfur Amino Acid Intake on Immune Function in Humans, J. Nutr, Jun. 2006, vol. 136, No. 6 Suppl, 1660S-1665S.

PubMed Abstract for Johannessen, L.N., et al.; Mycotoxin-induced depletion of intracellular glutathione and altered cytokine production in the human alveolar epithelial cell line A549, Toxicol Letters, Jan. 30, 2007; 168(2):103-12.

PubMed Abstract for Maggi, L., et al.; Transformation ability of fungi isolated from cork and grape to produce 2, 4, 6-trichloroanisole from 2, 4, 6-trichlorophenol, Food Additives and Contaminants Part A Chem Anal Control Expo Risk Assess, Mar. 2008; 25(3):265-9.

PubMed Abstract for Davutoglu, M., et al.; Oxidative stress and antioxidant status in neonatal hyperbilirubinemia, Saudi Med J., Dec. 2008; 29(12):1743-8.

PubMed Abstract for Stevenson, D.K., et al.; Metalloporphyrins in the management of neonatal hyperbilirubinemia, Semin Fetal Neonatal Med., Jun. 2010; 15(3):164-168.

PubMed Abstract for Turgut, M., et al.; Oxidant and antioxidant levels in preterm newborns with idiopathic hyperbilirubinaemia, J Paediatr Child Health, Nov. 2004; 40(11):633-7.

PubMed Abstract for Zachara, B.A., et al.; Red blood cell and plasma glutathione peroxidase activities and selenium concentration in patients with chronic kidney disease: a review, Acta Biochim Pol., 2006; 53(4):663-77.

PubMed Abstract for Davis, J.M., et al.; Maturation of the antioxidant system and the effects on preterm birth, Semin Neonatal Fetal Med., Aug. 2010; 15(4):191-5.

PubMed Abstract for Lee, J.W., et al.; Future applications of antioxidants in premature infants, Curr Opinion Ped, Apr. 2011; 23(2):161-6.

PubMed Abstract for Russell, G.A., Antioxidants and neonatal lung disease, Eur J Pediatr., 1994; 153(9 Suppl 2): S36-41.

PubMed Abstract for Majumder, S., et al.; Jaundice in new born and erythrocyte and plasma antioxidant defence system, Indian J Exper Biol., Apr. 1995; 33(4):303-5.

PubMed Abstract for Chessex, P., et al.; Determinants of oxidant stress in extremely low birth weight premature infants, Free Radic Biol Med., Nov. 15, 2010; 49(9):1380-6.

PubMed Abstract for Fu, R.N., et al.; Lower erythrocyte glutathione peroxidase activity in bronchopulmonary dysplasia in the first week of neonatal life, Neonatology, 2008; 93(4):269-75.

PubMed Abstract for Guarino, M.P., et al.; Hepatic glutathione and nitric oxide are critical for hepatic insulin-sensitizing substance action, Am J Physiol Gastrointest Liver Physiol, Apr. 2003; 284(4):G588-94.

Abstract for Baron, A.D., et al.; Insulin resistance after hypertension induced by the nitric oxide synthesis inhibitor L-NMMA in rats, Am J Physiol, Oct. 1995; 269(4 Pt 1):E709-15.

PubMed Abstract for Lauterburg, B.H.; Analgesics and Glutathione, Am. J. Ther. May-Jun. 2002; 9(3):225-33, Department of Clinical Pharmacology, University of Bern, Bern, Switzerland.

PubMed Abstract for Schultz, S.T., et al.; Acetaminophen use, measles-mumps-rubella vaccination, and autistic disorder, Autism 2008 vol. 12(3) 293-307.

PubMed Abstract for Bajt, M.L., et al.; Acetaminophen-Induced Oxidant Stress and Cell Injury in Cultured Mouse Hepatocytes: Protection by N-Acetyl Cysteine, Toxicological Sciences, 80, 343-349 (2004).

PubMed Abstract for Fernandez-Checa, J.C., et al.; Oxidative stress: Role of mitochondria and protection by glutathione, BioFactors, Issue vol. 8, Nos. 1-2/1998 pp. 7-11, 1, Instituto Investigaciones Biomedicas, Consejo Superior Investigaciones Cientaficas (CSIC), and Liver Unit, Department of Medicine, Hospital Clinic I Provincial, Barcelona, Spain.

PubMed Abstract for Marzullo, L.; An update of N-acetylcysteine treatment for acute acetaminophen toxicity in children, Curr. Opin. Pediatr. Apr. 2005; 17(2):239-45.

PubMed Abstract for Terneus, M., et al.; Comparison of S-Adenosyl-L-methionine and N-Acetylcysteine, Protective Effects on Acetaminophen Hepatic Toxicity, J. of Pharmacology and Experimental Therapeutics, Jan. 2007; 320(1):99-107.

(56) References Cited

OTHER PUBLICATIONS

PubMed Abstract for Shih, A.Y., et al.; Cystine/Glutamate Exchange Modulates Glutathione Supply for Neuroprotection from Oxidative Stress and Cell Proliferation, The Journal of Neuroscience, Oct. 11, 2006 26(41):10514-10523.

PubMed Abstract for Badaloo, A., et al.; Cysteine supplementation improves the erythrocyte glutathione synthesis rate in children with severe edematous malnutrition, Am J Clin Nutrition, Sep. 2002;76(3):646-52.

PubMed Abstract for Anderson, M.E., et al.; Glutathione metabolism at the blood-cerebrospinal fluid barrier, FASEB J., Nov. 1989;3(13):2527-31, Departments of Biochemistry and Neurobiology, Cornell University Medical College, NY, NY 10021.

PubMed Abstract for Kern, J.K., et al.; Evidence of Toxicity and Oxidative Stress and Neuronal Insult in Autism, Journal of Toxicology and Environmental Health, Part B, 9:485-499, 2006, Department of Psychiatry, University of Texas, Southwestern Medical Center at Dallas, Texas, USA.

PubMed Abstract for Ravindranath, V., et al.; Glutathione Depletion and Formation of Glutathione-Protein Mixed Disulfide Following Exposure of Brain Mitochondria to Oxidative Stress, Biochemical and Biophysical Research Communications, vol. 169, No. 3, Jun. 29, 1990, pp. 1075-I079.

PubMed Abstract for Johannessen, L.N., et al.; The mycotoxins citrinin and gliotoxin differentially affect production of the pro-inflammatory cytokines tumour necrosis factor-alpha and interleukin-6, and the anti-inflammatory cytokine interleukin-10, Clin. Exp. Allergy, Jun. 2005; 35(6):782-9, Department of Cancer Research and Molecular Medicine, Faculty of Medicine, Norwegian University of Science and Technology, Trondheim, Norway.

PubMed Abstract for Jaeschke, H., et al.; The role of oxidant stress and reactive nitrogen species in acetaminophen hepatotoxicity, Toxicology Letters, Oct. 15, 2003; 144(3):279-88.

PubMed Abstract for Shen, D., et al.; Glutathione Redox State Regulates Mitochondrial Reactive Oxygen Production, The Journal of Biological Chemistry, vol. 280, No. 27, Issue of Jul. 8, pp. 25305-25312, 2005.

PubMed Abstract for Sido, B., et al.; Impairment of intestinal glutathione synthesis in patients with inflammatory bowel disease, Gut Apr. 1998; 42(4):485-492.

PubMed Abstract for Chauhan, A., et al.; Oxidative stress in Autism, Pathophysiology, Aug. 2006; 13(3):171-181.

PubMed Abstract for Kromidas, L., et al.; The protective effects of glutathione against methyl mercury cytotoxicity, Toxicology Letters, vol. 51, Issue 1, Mar. 1990, pp. 67-80.

PubMed Abstract for Geier, D.A., et al.; Mitochondrial dysfunction, impaired oxidative-reduction activity, degeneration, and death in human neuronal and fetal cells induced by low-level exposure to thimerosal and other metal compounds, Toxicological & Environmental Chemistry, vol. 91, Issue 4, Jun. 2009, pp. 735-749.

PubMed Abstract for Shah, D.T., et al.; Clinical isolates of yeast produce a Gliotoxin-like substance, Mycopathologia, vol. 116, No. 3, Dec. 1991, pp. 203-208.

PubMed Abstract for Gardiner, D.M., et al.; The epipolythiodioxopiperazine (ETP) class of fungal toxins: distribution, mode of action, functions and biosynthesis, Microbiology Apr. 2005, 151(4), 1021-1032.

PubMed Abstract for Stanzani, M., et al.; Aspergillus fumigatus suppresses the human cellular immune response via gliotoxin-mediated apoptosis of monocytes, Blood, Mar. 15, 2005; 105(6):2258-2265.

PubMed Abstract for Lewis, R.E., et al.; Frequency and Species Distribution of Gliotoxin-Producing Aspergillus Isolates Recovered from Patients at a Tertiary-Care Cancer Center, Journal of Clinical Microbiology, Dec. 2005, 43 (12):6120-6126.

PubMed Abstract for Pahl, H.L., et al.; The Immunosupressive Fungal Metabolite Gliotoxin Specifically Inhibits Transcription Factor NF-kB, J. Exp. Med., vol. 183(4), Apr. 1996, pp. 1829-1840.

PubMed Abstract for Jyonouchi, H., et al.; Dysregulated Innate Immune Responses in Young Children with Autism Spectrum Disorders: Their Relationship to Gastrointestinal Symptoms and Dietary Intervention, Neuropsychobiology 2005; 51(2):77-85.

PubMed Abstract for Shah, D.T., et al.; Effect of Gliotoxin on Human Polymorphonuclear Neutrophils, Infectious Diseases in Obstetrics and Gynecology, 6(4):168-175 (1998).

PubMed Abstract for Eichner, R.D., et al; Gliotoxin Causes Oxidative Damage to Plasmid and Cellular DNA, The Journal of Biological Chemistry, vol. 263, No. 8, Mar. 15, pp. 3772-3777, 1988.

PubMed Abstract for Brennan, L., et al.; Gliotoxins disrupt alanine metabolism and glutathione production in C6 glioma cells: a 13C NMR spectroscopic study, Neurochemistry International, Dec. 2004, 45 (8):1155-1165.

PubMed Abstract for Mullbacher, A., et al.; Immunosupression in vitro by a metabolite of a human pathogenic fungus, Proc. National Academy Science, USA, vol. 81(12), pp. 3835-3837, Jun. 1984.

PubMed Abstract for Kupfahl, C., et al.; Gliotoxin production by clinical and environmental *Aspergillus fumigatus* strains, International Journal of Medical Microbiology, vol. 298, Issues 3-4, Apr. 1, 2008, pp. 319-327.

PubMed Abstract for Lewis, R.E., et al.; Detection of Gliotoxin in Experimental and Human Aspergillosis, Infection and Immunity, Jan. 2005, p. 635-637, vol. 73, No. 1.

PubMed Abstract for Waring, P., et al.; Gliotoxin inactivates alcohol dehydrogenase by either covalent modification or free radical damage mediated by redox cycling, Biochem Pharmacology May 11, 1995; 49(9):1195-201, John Curtin School of Medical Research, Australian National University, Canberra City.

PubMed Abstract for Tsunawaki, S., et al.; Fungal Metabolite Gliotoxin Inhibits Assembly of the Human Respiratory Burst NADPH Oxidase, Infection and Immunity, Jun. 2004, 72(6), p. 3373-3382.

PubMed Abstract for Hurne, A.M., et al.; Inactivation of Rabbit Muscle Creatine Kinase by Reversible Formation of an Internal Disulfide Bond Induced by the Fungal Toxin Gliotoxin, The Journal of Biological Chemistry, vol. 275, No. 33, Issue of Aug. 18, 2000, pp. 25202-25206.

PubMed Abstract for Bernardo, P.H., et al.; Evidence for Gliotoxin-Glutathione Conjugate Adducts, Bioorganic & Medicinal Chemistry Letters, Feb. 26, 2001; 11(4):483-485.

PubMed Abstract for Bernardo, P.H., et al.; A Novel Redox Mechanism for the Glutathione-dependent Reversible Uptake of a Fungal Toxin in Cells, The Journal of Biological Chemistry, vol. 278, No. 47, Issue of Nov. 21, pp. 44549-46555, 2003.

PubMed Abstract for Axelsson, V., et al.; Glutathione intensifies gliotoxin-induced cytotoxicity in human neuroblastoma SH-SY5Y cells, Cell Biology and Toxicology, Mar. 2006; 22(2):127-136.

PubMed Abstract for Trown, P.W., et al.; Mechanism of Action of Gliotoxin: Elimination of Activity by Sulfhydryl Compounds, Antimicrobial Agents and Chemotherapy, Oct. 1972, p. 261-266. vol. 2, No. 4.

PubMed Abstract for Russo, A.J.; Anti-metallothionein IgG and levels of metallothionein in autistic children with GI disease, Drug Health Patient Safety 2009; 1:1-8., Mount Saint Mary's University, Emmitsburg, MD, USA.

PubMed Abstract for Liu, J., et al.; Metallothionein-I/II Knockout Mice are Sensitive to Acetaminophen-Induced Hepatotoxicity, The Journal of Pharmacology and Experimental Therapeutics, Apr. 1999; 289(1): 580-586.

PubMed Abstract for Andrews, G.K.; Regulation of Metallothionein Gene Expression by Oxidative Stress and Metal Ions, Biochemical Pharmacology, Jan. 1, 2000; 59(1), pp. 95-104.

PubMed Abstract for Maret, W.; Oxidative metal release from metallothionein via zinc-thiol/disulfide interchange, Proc. Natl. Acad. Sci. USA, vol. 91(1), pp. 237-241, Jan. 4, 1994.

PubMed Abstract for Maret, W.; The Function of Zinc Metallothionein: A Link between Cellular Zinc and Re-dox State, The Journal of Nutrition, May 2000; 130(5S Suppl.):1455S-8S.

PubMed Abstract for Jacob, C., et al.; Control of zinc transfer between thionein, metallothionein, and zinc proteins, Proc Natl Acad Sci, USA, Mar. 31, 1998; 95(7):3489-94.

(56) References Cited

OTHER PUBLICATIONS

PubMed Abstract for Aschner, M., et al.; Metallothioneins: Mercury Species—Specific Induction and Their Potential Role in Attenuating Neurotoxicity, Exp Biol Med (Maywood), Oct. 2006; 231(9):1468-73.
PubMed Abstract for McFadden, S.A.; Phenotypic variation in xenophobic metabolism and adverse environmental response: focus on sulfur-dependent detoxification pathways, Toxicology, Jul. 17, 1996; 111(1-3):43-65.
PubMed Abstract for Sheline, C.T., et al.; Zinc-Induced Cortical Neuronal Death: Contribution of Energy Failure Attributable to Loss of NAD and Inhibition of Glycolysis, The Journal of Neuroscience, May 1, 2000; 20 (9): 3139-3146.
PubMed Abstract for Gazaryan, I.G., et al.; Zinc Irreversibly Damages Major Enzymes of Energy Production and Antioxidant Defense Prior to Mitochondrial Permeability Transition, Journal of Biological Chemistry, vol. 282, Issue 33, 24373-24380, Aug. 17, 2007.
PubMed Abstract for Yamasaki, S., et al.; Zinc is a novel intracellular second messenger, The Journal of Cell Biology, May 21, 2007; vol. 177, No. 4, 637-645.
PubMed Abstract for Kern, J.K., et al.; Sulfhydryl-Reactive Metals in Autism, Journal of Toxicology and Environmental Health, Part A, Apr. 15, 2007; 70(8): 715-721.
PubMed Abstract for LoPachin, R.M., et al.; Synaptic Cysteine Sulfhydryl Groups as Targets of Electrophilic Neurotoxicants, Toxicological Sciences, Dec. 2006; 94 (2), 240-255.
PubMed Abstract for Allen, J.W., et al.; The Consequences of Methylmercury Exposure on Interactive Functions between Astrocytes and Neurons, Neurotoxicology, Dec. 2002; 23(6):755-759.
PubMed Abstract for James, S.J., et al.; Thimerosol Neurotoxicity is Associated with Glutathione Depletion: Protection with Glutathione Precursors, Neurotoxicology, Jan. 2005; 26(1):1-8.
PubMed Abstract for Aon, M.A., et al.; Sequential Opening of Mitochondrial Ion Channels as a Function of Glutathione Re-dox Thiol Status, The Journal of Biological Chemistry, vol. 282, No. 30, pp. 21889-21900, Jul. 27, 2007.
PubMed Abstract for Dameron, C.T., et al.; Glutathione-coated Cadmium-Sulfide Crystallites in Candida Glabrata, J Biol Chem, Oct. 15, 1989; 264(29):17355-60, Departments of Medicine and Biochemistry, University of Utah Medical Center, Salt Lake City, Utah 84132.
PubMed Abstract for Li, L., et al.; Candida Glabrata, an Emerging Oral Opportunistic Pathogen, J Dent Res, Mar. 2007; 86(3):204-15, Department of Oral Health and Diagnostic Sciences, School of Dental Medicine, Univ. of Connecticut, Farmington, CT 06030-1710, USA; and Dept of General Dentistry, School of Dentistry, Univ. of Texas Health Science Center at San Antonio, San Antonio, TX 78229-3900, USA.
PubMed Abstract for Austin, N., et al.; Prophylactic systemic antifungal agents to prevent mortality and morbidity in very low birth weight infants, Cochrane Database Syst Rev., Apr. 30, 2013; 4:CDO03850.
PubMed Abstract for Noverr, M.C., et al.; Pathogenic Yeasts Cryptococcus neoformans and Candida albicans Produce Immunomodulatory Prostaglandins, Infect Immun, May 2001; 69(5):2957-63, Division of Pulmonary and Critical Care Medicine, Department of Internal Medicine, and Department of Microbiology and Immunology, University of Michigan Medical School, Ann Arbor, Michigan 48109-0642.
PubMed Abstract for Campa, A., et al.; Mortality risk in selenium-deficient HIV-positive children, J Acquir Immune Defic Syndr Hum Retrovirol, Apr. 15, 1999; 20(5):508-13, Center for Disease Prevention, Department of Psychiatry and Behavioral Sciences, University of Miami School of Medicine, Florida 33136, USA.
PubMed Abstract for Mullbacher, A., et al.; Immunosuppression in vitro by a metabolite of a human pathogenic fungus, Proc Natl Acad Sci USA, vol. 81(12), pp. 3835-3837, Jun. 1984, Dept. of Microbiology and Immunology, John Curtin School of Medical Research, Australian National University, Canberra, A.C.T. 2601, Australia.
PubMed Abstract for Soerensen, J., et al.; The role of thioredoxin reductases in brain development, PLoS One, Mar. 19, 2008; 3(3):e1813, Department of Comparative Medicine, Helmholtz Zentrum München German Research Center for Environmental Health, Neuherberg, Germany.
PubMed Abstract for Ivanovski, O., et al.; The antioxidant N-acetylcysteine prevents accelerated atherosclerosis in uremic apolipoprotein E knockout mice, Kidney Int., Jun. 2005; 67(6):2288-94, INSERM Unit 507, Necker Hospital, Paris, France.
PubMed Abstract for Waring, P.; DNA fragmentation induced in macrophages by Gliotoxin does not require protein synthesis and is preceded by raised inositol triphosphate levels, J Biol Chem, Aug. 25, 1990; 265(24):14476-80, Division of Cell Biology, John Curtin School of Medical Research, Australian National University, Canberra.
PubMed Abstract for Staib, F., et al.; The p53 tumor suppressor network is a key responder to microenvironmental components of chronic inflammatory stress, Cancer Res, Nov. 15, 2005; 65(22):10255-64, Laboratories of Human Carcinogenesis, Center for Cancer Research, National Cancer Institute, NIH, Bethesda, Maryland 20892-4255, USA.
PubMed Abstract for Pena, G.A., et al.; Aspergillus fumigatus toxicity and gliotoxin levels in feedstuff for domestic animals and pets in Argentina, Letters in Applied Microbiology, Jan. 2010; 50(1):77-81.
PubMed Abstract for Franck, L., et al.; Infant Sleep after Immunization: Randomized Controlled Trial of Prophylactic Acetaminophen, Pediatrics, Dec. 2011; 128(6):1100-8.
PubMed Abstract for Kwon-Chung, K.J., et al.; What do we know about the role of Gliotoxin in the pathobiology of Aspergillus fumigatus?, Med Mycol, 2009; 47 (Suppl.1): S97-103, Molecular Microbiology Section, Laboratory of Clinical Infectious Diseases, National Institute of Allergy and Infectious Diseases, National Institutes of Health, Bethesda, Maryland, USA.
PubMed Abstract for Kamei, K., et al.; Aspergillus mycotoxins and their effect on the host, Medical Mycology, May 2005; 43 Suppl 1:S95-9, Research Center for Pathogenic Fungi and Microbial Toxicoses, Chiba University, Japan.
PubMed Abstract for Adams, J.B., et al.; Safety and efficacy of oral DMSA therapy for children with autism spectrum disorders: Part A—Medical results, BMC Clinical Pharmacology, Oct. 23, 2009; 1472-6904-9-16, Division of Basic Medical Sciences, Southwest College of Naturopathic Medicine, Tempe, AZ, USA.
PubMed Abstract for De Mattia, G., et al.; Influence of reduced glutathione infusion on glucose metabolism in patients with non-insulin-dependent diabetes mellitus, Metabolism, Aug. 1998;47(8):993-7.
PubMed Abstract for De Mattia, G., et al.; Reduction of oxidative stress by oral N-acetyl-L-cysteine treatment decreases plasma soluble vascular cell adhesion molecule-1 concentrations in non-obese, non-dyslipidaemic, normotensive, patients with non-insulin-dependent diabetes, Diabetologia, Nov. 1998; 41(11):1392-6.
PubMed Abstract for Samiec, P.S., et al.; Glutathione in human plasma: decline in association with aging, age-related macular degeneration, and diabetes, Free Radic Biol Med, Mar. 15, 1998; 24(5):699-704.
PubMed Abstract for Cohen, S.M., et al.; Low glutathione reductase and peroxidase activity in age-related macular degeneration, Br J Opthalmol, Oct. 1994; 78(10):791-4.
PubMed Abstract for Evereklioglu, C., et al.; Nitric oxide and lipid peroxidation are increased and associated with decreased antioxidant enzyme activities in patients with age-related macular degeneration, Doc Opthalmol, Mar. 2003; 106(2):129-36.
PubMed Abstract for Likidlilid, A., et al.; Lipid peroxidation and antioxidant enzyme activities in erythrocytes of type 2 diabetic patients, J Med Assoc Thai, Jun. 2010; 93(6):682-93.
PubMed Abstract for Ciobica, A., et al.; Oxidative stress in schizophrenia—focusing on the main markers, Psychiatr Danub, Sep. 2011; 23(3):237-45.

(56) References Cited

OTHER PUBLICATIONS

PubMed Abstract for Fendri, C., et al.; [Oxidative stress involvement in schizophrenia pathophysiology: a review], [Article in French], Encephale, Mar.-Apr. 2006; 32(2 Pt 1)244-52.
PubMed Abstract for Albarracin, S.L., et al.; Effects of natural antioxidants in neurodegenerative disease, Nutr Neurosci, Jan. 2012; 15(1):1-9.
PubMed Abstract for Zhao, B., Natural antioxidants protect neurons in Alzheimer's disease and Parkinson's disease, Neurochem Res, Apr. 2009; 34(4):630-8.
PubMed Abstract for Di Matteo, V., et al.; Biochemical and therapeutic effects of antioxidants in the treatment of Alzheimer's disease, Parkinson's disease, and amyotrophic lateral sclerosis, Curr Drug Targets CNS Neurol Disord, Apr. 2003; 2(2):95-107.
PubMed Abstract for Foster, M., et al.; Zinc and redox signaling: perturbations associated with cardiovascular disease and diabetes mellitus, Antioxid Redox Signal, Nov. 15, 2010; 13(10):1549-73.
PubMed Abstract for Lash, L.H., Renal membrane transport of glutathione in toxicology and disease, Vet Pathol, Mar. 2011; 48(2):408-19.
PubMed Abstract for Montazerifar, F., et al.; Evaluation of lipid peroxidation and erythrocyte glutathione peroxidase and superoxide dismutase in hemodialysis patients, Saudi J Kidney Dis Transpl, Mar. 2012; 23(2):274-9.
PubMed Abstract for Chiavaroli, V., et al.; Unbalanced oxidant-antioxidant status and its effects in pediatric diseases, Redox Rep, 2011; 16(3):101-7.
PubMed Abstract for Nadeem, A.; Oxidant—antioxidant imbalance in asthma: scientific evidence, epidemiological data and possible therapeutic options, Ther Adv Resp Dis, Aug. 2008;2(4):215-35.
PubMed Abstract for Mitchell, J.B., et al.; The role of glutathione in radiation and drug induced cytotoxicity, Br J Cancer Suppl, Jun. 8, 1987:96-104.
PubMed Abstract for Partlo, L.A., et al.; Effects of repeated hydrogen sulphide (H2S) exposure on learning and memory in the adult rat, Neurotoxicology, Apr. 2001;22(2):177-89.
PubMed Abstract for Guidotti, T.L., Hydrogen sulphide, Occup Med, London, Oct. 1996;46(5):367-71.
International Search Report dated Jan. 25, 2013 issued in corresponding International patent application No. PCT/US2012/043161.
S. Jill James et al., The FASEB Journal, Mar. 23, 2009, vol. 23, No. 8, pp. 2374-2383.
S. Jill James et al., The American Journal of Clinical Nutrition, 2004, vol. 80, No. 6, pp. 1611-1617.
PubMed Abstract for Bertling, A., et al.; Candida Albicans and its metabolite gliotoxin inhibit platelet function via interaction with thiols, Thrombosis Haemost, Aug. 2010; 104(2):270-8, Department of Anaesthesiology and Intensive Care, Experimental and Clinical Haemostasis, University of Muenster, Muenster, Germany.
PubMed Abstract for Folkerth, R.D.; Neuropathologic Substrate of Cerebral Palsy, Journal of Child Neurology, Dec. 2005; vol. 20, No. 12, pp. 940-949.
PubMed Abstract for Wu, Y.W., et al.; Chorioamnionitis as a risk factor for Cerebral Palsy: A meta-analysis, JAMA Sep. 20, 2000; 248(11):1417-1424.
PubMed Abstract for Dammann, O., et al.; Perinatal infection, inflammatory response, white matter damage, and cognitive limitations in children born preterm, Ment Retard Dev Disabil Res Rev, 2002; 8(1):46-50.
PubMed Abstract for Back, S.A., et al.; Maturation-dependent vulnerability of oligodendrocytes to oxidative stress-induced death caused by glutathione depletion, J. Neuroscience, Aug. 15, 1998; 18(16):6241-6253.
PubMed Abstract for Yoon, B.H., et al.; High expression of tumor necrosis factor-alpha and interleukin-6 in periventricular leukomalacia, Am J Obstet Gynecol Aug. 1997; 177(2):406-411.

PubMed Abstract for Folkerth, R.D., et al.; Oxidative Injury in the Cerebral Cortex and Subplate Neurons in Periventricular Leukomalacia, J Neuropathol Exp Neurol., Jul. 2008; 67(7): 677-686.
PubMed Abstract for Baud, O., et al.; Developmental Regulation of manganese superoxide dismutase in rat oligodendrocytes confers protection against glutathione depletion induced toxicity, Eur J Neurosci, Jul. 2004: 20(1):29-40.
PubMed Abstract for Glass, H.C., et al.; Recurrent postnatal infections are associated with progressive white matter injury in premature infants, Pediatrics, Aug. 2008; 122(2):299-305, Department of Neurology, University of California, San Francisco, USA.
PubMed Abstract for Friedman, S., et al.; Systemic Candida infection in extremely low birth weight infants: short term morbidity and long term neurodevelopmental outcome, Pediatr Infect Dis J, Jun. 2000; 19(6):499-504, Pediatric Infectious Disease, Department of Pediatrics, The Hospital for Sick Children, Toronto, Ontario, Canada.
PubMed Abstract for Baud, O., et al.; [Maternofetal disseminated candidiasis and high-grade prematurity] [Article in French], Archives Pediatrics, Apr. 1997; 4(4):331-4, Service de pédiatrie et réanimation néonatales, hôpital Antoine-Béclère, Clamart, France.
PubMed Abstract for Austin, N.C., et al.; Prophylactic oral antifungal agents to prevent systemic Candida infection in preterm infants, Cochrane Database Syst Rev, 2004; (1): CD003478, Neonatal Intensive Care Unit, Christchurch Women's Hospital, Christchurch, New Zealand.
PubMed Abstract for Dammann, O., et al.; Is periventricular leukomalacia an axonopathy as well as an oligopathy?, Pediatr Res., Apr. 2001; 49(4):453-7, Neuroepidemiology Unit, Department of Neurology, Children's Hospital, Boston, Massachusetts 02115, U.S.A.
PubMed Abstract for Verma, U., et al,; Obstetric antecedents of intraventricular hemorrhage and periventricular leukomalacia in the low-birth-weight neonate, AM J Obstet Gynecol, Feb. 1997; 176(2):275-81, Department of Obstetrics and Gynecology, New York Medical College, Westchester County Medical Center, Valhalla 10595, USA.
PubMed Abstract for Speth, C., et al.; Gliotoxin as putative virulence factor and immunotherapeutic target in a cell culture model of cerebral aspergillosis, Mol Immunol., Sep. 2011; 48(15-16):2122-9, Department of Hygiene, Microbiology and Social Medicine, Innsbruck Medical University, Innsbruck, Austria.
PubMed Abstract for Eichner, R.D., et al.; Gliotoxin causes oxidative damage to plasmid and cellular DNA, J Biol Chem., Mar. 15, 1998; 263(8):3772-7.
PubMed Abstract for Trown, P.W., et al.; Mechanism of action of gliotoxin: elimination of activity by sulfhydryl compounds, Antimicrob Agents Chemother., Oct. 1972; 2(4):261-6.
PubMed Abstract for Glass, H.C., et al.; Recurrent postnatal infections are associated with progressive white matter injury in premature infants, Pediatrics, Aug. 2008; 122(2):299-305.
PubMed Abstract for Carberry, S., et al.; Gliotoxin effects on fungal growth: mechanisms and exploitation, Fungal Genet Biol., Apr. 2012; 49(4):302-12.
PubMed Abstract for Davis, C., et al.; Single-pot derivatisation strategy for enhanced gliotoxin detection by HPLC and MALDI-ToF mass spectrometry, Anal Bioanal Chem., Nov. 2011; 401(8):2519-29.
PubMed Abstract for Reeves, E.P., et al.; Effect of N-chlorotaurine on Aspergillus, with particular reference to destruction of secreted gliotoxin, J. Med. Microbiology, Jul. 2006; 55 (Pt 7):913-8, Medical Mycology Unit, National Institute for Cellular Biotechnology, Department of Biology, NUI Maynooth, Co. Kildare, Ireland.
PubMed Abstract for Reeves, E.P., et al.; Amphotericin B enhances the synthesis and release of the immunosuppressive agent gliotoxin from the pulmonary pathogen Aspergillus fumigatus, J. Med. Microbiology, Aug. 2004; 53(Pt 8):719-25.
PubMed Abstract for Fox, M., et al.; Detection of Aspergillus fumigatus mycotoxins: immunogen synthesis and immunoassay development, J. Micrbiol Methods, Feb. 2004; 56(2):221-30,

(56) References Cited

OTHER PUBLICATIONS

National Institute for Cellular Biotechnology, Department of Biology, National University of Ireland Maynooth, Maynooth, Co. Kildare, Ireland.

PubMed Abstract for Kontoyiannis, D.P.; Manipulation of host angioneogenesis: A critical link for understanding the pathogenesis of invasive mold infections?, Virulence, May-Jun. 2010; 1(3):192-6, Department of Infectious Diseases, Infection Control and Employee Health, The University of Texas MD Anderson Cancer Center, Houston, TX, USA.

PubMed Abstract for Stanzani, M., et al.; Aspergillus fumigatus suppresses the human cellular immune response via gliotoxin-mediated apoptosis of monocytes, Blood, Mar. 15, 2005; 105(6):2258-65, Transplant Immunology Section, Department of Blood and Marrow Transplantation, MD Anderson Cancer Center, SCRB 3.3019, Unit 900, 7455 Fannin St, Houston, TX 77030, USA.

PubMed Abstract for Penkowa, M., et al.; Increased astrocytic expression of metallothioneins I + II in brainstem of adult rats treated with 6-aminonicotinamide, Brain Research, Nov. 7, 1997; 774(1-2):256-9, Dept. of Medical Anatomy, The Panum Institute, Univ. of Copenhagen, Denmark.

PubMed Abstract for Penkowa, M., et al.; Metallothionein prevents neurodegeneration and central nervous system cell death after treatment with gliotoxin 6-aminonicotinamide, J. Neuroscience Res, Jul. 1, 2004; 77(1):35-53, Department of Medical Anatomy, The Panum Institute, University of Copenhagen, Copenhagen, Denmark.

PubMed Abstract for Russo, A.F., Anti-metallothionein IgG and levels of metallothionein in Autistic families, Swiss Medical Weekly, Feb. 9, 2008; 138(5-6):70-7, Science Department, Mount Saint Mary's University, Emmitsburg, MD 21727, USA.

PubMed Abstract for Keller, L.A., et al.; Gliotoxin contamination in and pre- and post-fermented corn, sorghum and wet brewer's grains silage in Sao Paulo and Rio de Janeiro State, Brazil, J. Appl. Microbiology, May 2012; 112 (5):865-73.

PubMed Abstract for Negi, R., et al.; Trace elements and antioxidant enzymes associated with oxidative stress in the pre-eclamptic/eclamptic mothers during fetal circulation, Clin Nutr., Dec. 2012, 31(6):946-50.

PubMed Abstract for Howlader, M.Z., et al.; Oxidative stress and antioxidant status in neonates born to pre-eclamptic mother, J Trop Pedatrics, Dec. 2009; 55(6):363-7.

PubMed Abstract for Siddiqui, I.A., et al.; Role of oxidative stress in the pathogenesis of preeclampsia, Arch Gynecol Obstet., Nov. 2010; 282(5):469-74.

PubMed Abstract for Johnstone, E.D., et al.; Differential proteomic analysis of highly purified placental cytotrophoblasts in pre-eclampsia demonstrates a state of increased oxidative stress and reduced cytotrophoblast antioxidant defense, Proteonomics, Oct. 11, 2011(20):4077-84.

PubMed Abstract for Rani, N., et al.; Role of oxidative stress markers and antioxidants in the placenta of preeclamptic patients, J Obstet Gynaecol Res, Dec. 2010; 36 (6):1189-94.

PubMed Abstract for Lopez-Tinoco, C., et al.; Oxidative stress and antioxidant status in patients with late-onset gestational diabetes mellitus, Acta Diabeto., Apr. 2013; 50(2):201-8.

PubMed Abstract for Lappas, M., et al.; The role of oxidative stress in the pathophysiology of gestational diabetes mellitus, Antioxid Redox Signal, Dec. 15, 2011; 15(12):3061-100.

PubMed Abstract for Coughlan, M.T., et al.; Altered placental oxidative stress status in gestational diabetes mellitus, Jan. 2004; 25(1):78-84.

Abstract for Farrell, S.E., et. al.; Toxicity of Acetaminophen, Medscape Reference, Jun. 24, 2014, Asst. Prof. of Medicine, Harvard Med. School; Dept. of Emergency Medicine, Brigham and Women's Hospital., Boston, Mass.

Abstract for Horvath, K., et al.; Abnormal Sulfate Metabolism in Autism, Journal of Pediatric Gastroenterology and Nutrition, vol. 39, Jun. 2004.

Abstract for Shathele, M.S., Effect of Administration of fungal toxin (Gliotoxin) in Clinical and Serobiochemical Parameters in Camels, International Journal of Pharmacology, 2009; 5(6):381-383, Dept of Microbiology, King Faisal University.

Abstract for: Study of Glutathione, Vitamin C and Cysteine in Children With Autism and Severe Behavior Problems, US Clinical Trial Registry, Jan. 2011, University of Louisville, Kosair Children's Hospital Foundation, Cumberland Pharmaceuticals.

Abstract for Rowen, J.L., et al.; Candida Isolates from Neonates: Frequency of Misidentification and Reduced Fluconazole Susceptibility, J. Clin. Microbiol., Nov. 1999; 37(11):3735-3737.

Abstract for Nichea, M.J., et al.; Presence of Multiple Mycotoxins and Other Fungal Metabolites in Native Grasses from a Wetland Ecosystem in Argentina Intended for Grazing Cattle, Toxins (Basel), Aug. 20, 2015; 7(8):3309-29.

Bennett, J.W., et al.; Mycotoxins, Clin. Microbiol. Rev., Jul. 2003; 16(3):497-516.

Abstract for Brouillet, E., et al.; Age-dependent vulnerability of the striatum to the mitochondrial toxin 3-nitropropionic acid, J. Neurochem., Jan. 1993; 60(1):356-9.

Kwon-Chung, K.J., et al.; What do we know about the role of gliotoxin in the pathobiology of Aspergillus fumigatus?, Med. Mycol., 2009; 47 Suppl 1:S97-103.

Abstract for Owens, R.A., et al.; Interplay between Gliotoxin Resistance, Secretion, and the Methyl/Methionine Cycle in Aspergillus fumigatus, Eukaryot Cell., Sep. 2015; 14(9):941-57.

Abstract for Kamei, K., et al.; Aspergillus mycotoxins and their effect on the host, Med. Mycol., May 2005; 43 Suppl 1: S95-9.

Abstract for Amitani, R., et al.; Purification and characterization of factors produced by Aspergillus fumigatus which affect human ciliated respiratory epithelium, Infect. Immun., Sep. 1995; 63(9):3266-71.

Abstract for Waring, P., et al.; The possible role of gliotoxin in health and disease, Endeavour, 1992; 16(1):14-6.

Abstract for Bugli, F., et al.; Increased production of gliotoxin is related to the formation of biofilm by Aspergillus fumigatus: an immunological approach, Pathog. Dis., Apr. 2014; 70(3):379-89.

Abstract for Kupfahl, C., et al.; Gliotoxin production by clinical and environmental *Aspergillus fumigatus* strains, Med. Microbiol., Apr. 2008; 298(3-4):319-27.

Abstract for Mueller, A., et al.; Individual and combined effects of mycotoxins from typical indoor moulds, Toxicol. In Vitro., Sep. 2013; 27(6):1970-8.

Abstract for El-Ansary, A.K., et al.; On the protective effect of omega-3 against propionic acid-induced neurotoxicity in rat pups, Lipids Health Dis., Aug. 19, 2011; 10:142.

Abstract for El-Ansary, A.K., et al.; Etiology of autistic features: the persisting neurotoxic effects of propionic acid, J Neuroinflammation, Apr. 24, 2012; 9:74.

Abstract for Dan, M.C.T., et al.; Colonic Fermentation of Unavailable Carbohydrates from Unripe Banana and its Influence over Glycemic Control, Springer, Sep. 2015; vol. 70, Issue 3, pp. 297-303; First online: Jun. 20, 2015.

Abstract for Alfawaz, H.A., et al.; Protective and restorative potency of Vitamin D on persistent biochemical autistic features induced in propionic acid-intoxicated rat pups, BMC Complement Altern. Med., 2014; 14: 416; Published online: Oct. 25, 2014.

Abstract for Pagan, C., et al.; The serotonin-N-acetylserotonin-melatonin pathway as a biomarker for autism spectrum disorders, Transl. Psychiatry, Nov. 11, 2014; 4:e479.

Abstract for Deepmala, et al.; Clinical trials of N-acetylcysteine in psychiatry and neurology: A systematic review, Neurosci. Biobehav. Rev., Aug. 2015; 55:294-321.

Schmitt, B., et al.; Effects of N-acetylcysteine,oralglutathione (GSH) and a novel sublingual form of GSH on oxidative stress markers: A comparative crossover study, Redox Biology 6, 2015; 198-205.

Bilbo, S.D., et al.; A model for the induction of autism in the ecosystem of the human body: the anatomy of a modern pandemic?, Microbial Ecology in Health & Disease, 2015; 26: 26253.

Jones, R.W., et al.; Mechanism of Gliotoxin Action and Factors Mediating Gliotoxin Sensitivity, Journal of General Microbiology, 1988; 134, 2067-2075.

(56) References Cited

OTHER PUBLICATIONS

Abstract for Axelsson, V., et al.; Glutathione intensifies gliotoxin-induced cytotoxicity in human neuroblastoma SH-SY5Y cells, Cell Biology and Toxicology, Mar. 2006; vol. 22, Issue 2, pp. 127-136; First online: Mar. 8, 2006.

Abstract for Bernardo, P.H., et al.; Evidence for Gliotoxin—Glutathione conjugate adducts, Bioorganic & Medicinal Chemistry Letters, Feb. 26, 2001; vol. 11, Issue 4, , pp. 483-485.

Trown, P.W., et al.; Mechanism of Action of Gliotoxin: Elimination of Activity by Sulfhydryl Compounds, Antimicrobial Agents and Chemotherapy, Oct. 1972; vol. 2, No. 4, p. 261-266.

Al-Dbass, A.M.; N-Acetylcysteine reduces the neurotoxic effects of propionic acid in rat pups, Journal of King Saud University—Science, 2014; 26:254-260.

Abstract for MacFabe, D.F., et al.; Neurobiological effects of intraventricular propionic acid in rats: Possible role of short chain fatty acids on the pathogenesis and characteristics of autism spectrum disorders, Behav Brain Res., Jan. 10, 2007; 176(1):149-69.

Abstract for Pocsi, I., et al.; Glutathione, Altruistic Metabolite in Fungi, Adv Microb Physiol., 2004; 49:1-76.

Pisa, D., et al.; Different Brain Regions are Infected with Fungi in Alzheimer's Disease, Sci. Rep., 5, 15015, Oct. 15, 2015 pp. 1-13 [online], [retrieved on Oct. 2005]. Retrieved from the Internet <URL: http://www.nature.com/articles/srep15015> <DOI: 10.1038/srep15015>.

METHODS FOR TREATMENT OF AUTISM

CROSS REFERENCE TO RELATED APPLICATIONS

The present application is a 35 U.S.C §§371 national phase conversion of PCT/US2012/043161, filed Jun. 19, 2012, claims the benefit of U.S. Provisional Patent Application No. 61/499,027, filed Jun. 20, 2011; the entire contents of which are hereby incorporated by reference herein.

TECHNICAL FIELD OF THE INVENTION

The present invention relates to mycotoxins and their role in disease etiology. The present invention is directed towards reducing human diseases, conditions, and states of morbidity and mortality by detecting and inhibiting production of harmful microbes and their toxins, and in particular pathogenic fungi and yeasts, in their human or other mammalian hosts. Mammalian species are prone to contamination by pathogenic fungi that produce toxic metabolites known as mycotoxins, and create other metabolic perturbations causing disease.

BACKGROUND OF THE INVENTION

The syndrome known as regressive autism is a multifaceted disease entity that can present with a multitude of protean manifestations that has defied an accepted definitive etiology to date. Common to many or most of these associated disease states is a generalized decrement in behavior and communication skills. Previously this deficiency has been attributed to heavy metal intoxication, among other suspected pathobiologies. The current invention describes actual pathogenic compounds known as mycotoxins, formed by yeasts, fungi and molds that infect and cause disease in mammals and eukaryotes. For instance, the mycotoxin gliotoxin, produced by *Candida, Aspergillus* and *Penicillium* species, among others, has been shown to rapidly bind to sulfur containing molecules and render many molecules and proteins and enzymes nonfunctional. Gliotoxin has also been shown to bind to, deplete, and oxidize glutathione, a crucial antioxidant, causing oxidative stress. Glutathione is also responsible for the effective function of the crucial enzyme systems known as metallothioneins, which are needed for metabolism and maintenance of crucial metals in the brain and other bodily sites. Aflatoxin is similarly produced by mycotoxigenic fungal species and is immunosuppressive, inhibits protein synthesis and is carcinogenic, and may be a co-factor in many of the same disease states.

SUMMARY OF THE INVENTION

The current invention is directed towards a rapid, reproducible test(s) for fungal virulence factors and associated affected compounds so that patients at risk for autism, cerebral palsy and other human diseases can be quickly identified and treated, and disease progression possibly prevented. This includes a multitude of test protocols for both the mycotoxin gliotoxin, and its relationship with glutathione, and relates the two molecules by a novel paradigm known as the Glutathione-Gliotoxin Index—(GGI) or the Disease/Disorder Susceptibility Index—(D/DSI). This relates the two molecules, with the ratio of glutathione in the preferred redox state divided by the concentration of gliotoxin present in the sample tested concurrently. Alternatively, the inverse ratio could be used, the Gliotoxin-Glutathione Index. These numerical relationships can be whole numbers, fractions, integers, decimals, and even negative numbers. The utility of said numerical ratios will be apparent when the full spectrums of aberrant toxicological and biochemical perturbations are apparent across the numerous disease states caused by this pathobiology. One testing protocol includes mass spectroscopy, including tandem mass spectroscopy, among many others. For instance, all bodily fluids and tissues are in the realm of a test paradigm for the toxigenic factor(s) and biochemical perturbations which cause neurobehavioral changes seen in autism and other disease states.

Of particular relevance for autism is the role of glutathione depletion by gliotoxin, then by the anti-pyretic acetaminophen in the peri-vaccination period, which each result in oxidative stress and metal intoxication, by disrupting the metallothionein system, amongst other biochemical pathways and enzyme systems. A numerical relationship between concentrations of glutathione and gliotoxin shall be known as the Autism Susceptibility Index—ASI.

The invention is also directed to prevention of said disease states by a multitude of methods such as competitive exclusion of gliotoxin producers by a non-toxigenic species, such as a beneficent pro-biotic. It is also directed towards treatment of said disease states by a fungistatic compound, a fungicidal compound, an ETP toxin antibody, a competitive inhibitor of said re-dox virulence factor by an antioxidant compound, a compound or element that neutralizes gliotoxin, such as selenium, zinc, manganese, taurine, and other minerals, enhancement of glutathione production by its precursor N-acetyl-cysteine, and addition of a toxin adsorbent to foodstuffs, among others.

It is therefore a general object of the invention to provide a novel testing paradigm, which will identify a potent fungal toxin, gliotoxin, or any epipolythiodioxopiperazine (ETP) toxin or mycotoxin, with negative public-health consequences in human disease.

It is another general object of the invention to provide novel paradigm relating the ratio of glutathione—reduced, oxidized or total—to the amount of gliotoxin present in a patient's samples. A related object of the invention is to provide a novel paradigm relating the presence and/or ratio of hydrogen sulfide present in a patient's sample. Such presence or ratio having implications with negative public-health consequences in human disease (and thus relevant for treatment, diagnosis or prevention of disease).

It is another general object of the invention to identify and quantify the Glutathione-Gliotoxin adducts and create a Glutathione-Gliotoxin Index—(GGI)—or the Disease/Disorder Susceptibility Index—(D/DSI), which also indicates the Autism Susceptibility Index—(ASI).

It is another general object of the invention to apply the GGI or D/DSI to a multitude of human diseases and conditions of current unknown etiology implicated by these indices so that said diseases can be prevented, treated and ameliorated.

It is a specific object of the invention to identify patients with a critical Autism Susceptibility Index—ASI—and to withhold acetaminophen from said patients to prevent onset of regressive autism.

It is a specific object of the invention to utilize a portable hand held electronic device, such as a cell phone, I-Pod, I-Pad, Android phone, or the like, with an attached or integrated module to test for said toxins, and a computer algorithm which computes levels of compounds tested for.

It will become apparent to one skilled in the art that said methods and processes will have inherent utility when a significant virulence factor in autism and other human diseases is tested for, treated, and the syndrome prevented, and said invention will have obvious value over the scant prior art.

One aspect is a method for determining susceptibility of a subject for autism, comprising: (a) measuring the level of glutathione in its reduced or oxidized state, or total glutathione in a sample from the subject; (b) measuring the level of gliotoxin in a sample from the subject; (c) calculating the Autism Susceptibility Index—(ASI) by calculating the ratio of the level of glutathione in the chosen state in (a) divided by the level of gliotoxin in (b); (d) where the ASI indicates susceptibility of the subject for Autism.

Other aspects include any of the methods herein:

further comprising communicating the ASI to a health care practitioner;

wherein the measuring of the levels of glutathione and gliotoxin (or any other compound being tested for, e.g., ETP, ETP metabolite, glutathione metabolite, hydrogen sulfide) are independently or concurrently performed using a method that is: high-pressure liquid chromatography (HPLC), reversed-phase liquid chromatography and HPLC, RP-HPLC/UV detection, thin-layer chromatography, radioimmunoassay (RIA), ETP antibody-linked RIA, ELISA, spectro-photometry, mass spectroscopy—MS, tandem MS, ES-MS, infrared spectroscopy, raman spectroscopy, lyophilized ligand-receptor complexes for assays and sensors, packed-flow cell fluorescence liquid chromatography (PFCFLC), antibody-linked immunoassay, adsorption chromatography, immuno-affinity chromatography, super-critical fluid extraction, bio-luminescence, chemical luminescence, NMR, isotopic S35 labeled quantification, radioactive scintillation, chiro-optical spectroscopy, polarimetry, optical rotatory dispersion, circular dichroism, circularly polarized luminescence, the use of Ellman's Reagent followed by UV-vis measurement, or any combination thereof;

wherein the sample is any bodily fluid, tissue, hair, stool, urine, cerebrospinal fluid—CSF, expired respiratory gas, or flatulence;

wherein the samples are erythrocytes;

wherein the glutathione is in its reduced state;

wherein the glutathione is in its oxidized state;

wherein the glutathione is its reduced or oxidized state or total glutathione, which is the sum of the oxidized and reduced glutathione;

wherein the glutathione is as an adduct with the ETP toxin (e.g., gliotoxin; any mycotoxin delineated herein);

wherein the ETP toxin (e.g., gliotoxin; any mycotoxin delineated herein) is as an adduct with glutathione;

wherein the communicating is performed via a portable communication device, scanner, electronic handheld device, cellular phone.

Another aspect is a method for determining susceptibility of a subject for autism, comprising: (a) applying to the subject optical radiation at a wavelength (e.g., any wavelength suitable to detect a compound; e.g., 50-600 nM) that will detect the level of glutathione in the preferred state in the subject; (b) detecting via optical radiation the level of glutathione in the preferred state in a subject; (c) applying to the subject optical radiation at a wavelength (e.g., any wavelength suitable to detect a compound; e.g., 50-600 nM) that will detect the level of gliotoxin in the subject; (d) applying to the subject radiation at a wavelength that will detect the level of the adducted Glutathione-Gliotoxin complexed in a subject. (e) detecting via optical radiation the level of gliotoxin in a subject ; (f) calculating the Autism Susceptibility Index—(ASI) by calculating the ratio of the level of glutathione detected in the chosen state (b) divided by the level of gliotoxin in (c); (g) where the ASI determined indicates susceptibility of the subject for autism.

Other aspects include any of the methods herein:

further comprising communicating the ASI to a health care practitioner;

wherein detecting comprises measuring the reflected optical radiation from aqueous and vitreous humor and retina of the eye;

wherein the communicating is via a portable communication device, scanner, electronic handheld device, or cellular phone.

Another aspect is a method for treating a subject comprising: (a) measuring the level of glutathione in its chosen state in a sample from the subject; (b) measuring the level of gliotoxin in a sample from the subject; (c) calculating the Autism Susceptibility Index—(ASI) by calculating the ratio of the level of glutathione in its chosen state in (a) divided by the level of gliotoxin in (b); (d) where the ASI level determined indicates a therapeutic intervention or administration of one or more agents to alter the ASI in the subject; (e) administration of nutritional supplementation, vitamins, minerals, amino acids, anti-oxidants, metal chelators, pharmacological intervention, antifungal, fungistatic, an ETP toxin antibody, pro-biotics, adsorbents, and introduction of non-glio-toxigenic species into said subject.

Another aspect is a device for monitoring a subject comprising: (a) a source for applying to the subject optical radiation at a wavelength that will detect the level of glutathione in the chosen state to the subject; (b) a detector for detecting via optical radiation the level of glutathione in the chosen state in a subject; (c) a source for applying to the subject optical radiation at a wavelength that will detect the level of gliotoxin in the subject; (d) a source for applying to the subject optical radiation at a wavelength that will detect the level of the adducted Glutathione-Gliotoxin complexed in a subject. (e) a detector for detecting via optical radiation the level of gliotoxin or adducted Glutathione-Gliotoxin in a subject.

Other aspects include any of the methods herein:

further comprising: a transmitter for communicating electronically information that is the levels of glutathione and gliotoxin detected, or information based on the levels of glutathione and gliotoxin detected.

Another aspect is a method of monitoring a subject comprising: (a) measuring the level of glutathione in the chosen state in a sample from the subject; (b) measuring the level of gliotoxin in a sample from the subject; (c) calculating the Autism Susceptibility Index—(ASI) by calculating the ratio of the level of glutathione in the preferred state (a) divided by the level of gliotoxin in (b); (d) where the ASI indicates susceptibility of the subject for autism.

Other aspects include any of the methods herein:

wherein the measuring is performed at periodic intervals;

wherein the measuring is performed pre-administration of any intervention measure or diagnostic enhancement intervention;

wherein the measuring is performed post-administration of any intervention measure or diagnostic enhancement intervention;

wherein the post-administration intervention measure is administration to the subject of one or more of nutritional supplementation, vitamins, minerals, amino acids, antioxidants, metal chelators, pharmacological intervention, antifungal, fungistatic, an ETP toxin antibody, adsorbents and introduction of non-toxigenic species into said subject.

Another aspect is a method for determining susceptibility of a subject for a disease, disorder, or symptom thereof, comprising: (a) measuring the level of glutathione in the preferred state in a sample from the subject; (b) measuring the level of an ETP toxin or mycotoxin in a sample from the subject; (c) calculating the Disease/Disorder Susceptibility Index—(D/DSI) or Glutathione/Gliotoxin Index—(G/GI) by calculating the ratio of the level of glutathione in its reduced, or oxidized, or total state in (a) divided by the level of ETP toxin or mycotoxin in (b); (d) where the D/DSI or G/GI indicates susceptibility of the subject for the disease, disorder, or symptom thereof.

Other aspects include any of the methods herein:

further comprising communicating the D/DSI or G/GI to a health care practitioner;

wherein the disease, disorder or symptom thereof is Cerebral Palsy, Periventricular Leukomalacia—PVL, Eclampsia-Preeclampsia, Pregnancy Induced Hypertension—PIH, Hypertension, HELLP Syndrome, Toxemia of Pregnancy, Gestational Diabetes, Diabetes, Anemia of pregnancy, HIV/AIDS, Cystic Fibrosis, Asthma, Cancer, Immunosuppression, atherosclerosis, dyslipidemia, renal disease, alcoholism, malnutrition, cirrhosis, hepatitis, Neonatal Jaundice, Bronchopulmonary Dysplasia, Multiple Sclerosis—MS, Macular Degeneration, Alzheimers disease, Parkinsonism, Amyotrophic Lateral Sclerosis, Schizophrenia, Ionizing Radiation Poisoning, and other diseases of Humans;

wherein the ETP toxin is one of Gliotoxin, Sirodesmin, Hyalodendrin, Spoidesmin A, Chaetomin, Chaetocin, Verticillins, Leptosin, Emestrin, Scabrosin, Dithiosilvatin, Epicorazine, Aranotin, or Emethallicin.

In another aspect, the invention is that wherein the Glutathione-Gliotoxin Index—(GGI) is determined from: (a) the level of glutathione in its chosen state (e.g., reduced, oxidized, reduced and oxidized combined) in a sample from the subject; and (b) the level of gliotoxin in a sample from the subject; by dividing the level of glutathione in its chosen state in (a) by the level of gliotoxin in (b). In embodiments, the GGI is a number (e.g., any number) wherein a GGI less than e.g., 1, 5, 10, 25, 100, 500, 1000, indicates susceptibility for a disease state. In embodiments, the GGI is a number (e.g., any number) wherein a GGI less than e.g., 0.001, 0.01, 0.1, 1, 5, 10, 25, 100, 500, 1000, indicates necessity for intervention for, treatment for, amelioration of, or prevention for a disease state in the subject.

In another aspect, the invention is that wherein the Disease/Disorder Susceptibility Index—(D/DSI) is determined from: (a) the level of glutathione in its chosen state (e.g., reduced, oxidized, reduced and oxidized combined) in a sample from the subject; and (b) the level of gliotoxin in a sample from the subject; by dividing the level of glutathione in its chosen state in (a) by the level of gliotoxin in (b). In embodiments, the D/DSI is a number (e.g., any number) wherein a D/DSI less than e.g., 1, 5, 10, 25, 100, 500, 1000, indicates susceptibility for a disease state. In embodiments, the D/DSI is a number (e.g., any number) wherein a D/DSI less than e.g., 0.001, 0.01, 0.1, 1, 5, 10, 25, 100, 500, 1000, indicates necessity for intervention, for treatment for, amelioration of, or prevention for a disease state in the subject.

In another aspect, the invention is that wherein the Autism Susceptibility Index—(ASI) is determined from: (a) the level of glutathione in its chosen state (e.g., reduced, oxidized, reduced and oxidized combined) in a sample from the subject; and (b) the level of gliotoxin in a sample from the subject; by dividing the level of glutathione in its chosen state in (a) by the level of gliotoxin in (b). In embodiments, the ASI is a number (e.g., any number) wherein a ASI less than e.g., 1, 5, 10, 25, 100, 500, 1000, indicates susceptibility for autism. In embodiments, the ASI is a number (e.g., any number) wherein a ASI less than e.g., 0.001, 0.01, 0.1, 1, 5, 10, 25, 100, 500, 1000, indicates necessity for intervention for, treatment for, amelioration of, or prevention for autism in the subject.

In another aspect, the invention provides identification of pathogenic compounds and perturbations from said compounds in said diseases and to intervene in said patients through therapeutic interventions to ameliorate or prevent such disease states.

DETAILED DESCRIPTION

Compounds and Definitions

Unless otherwise stated, chemical compounds and structures recited or depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The compounds delineated herein are commercially available from and/or can be synthesized using standard methods and reagents known in the art. The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development", Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Description of Exemplary Compounds

Compounds useful in the methods herein include, for example, nutritional supplements, vitamins, minerals, amino acids, anti-oxidants, metal chelators, pharmacological intervention, anti-fungal or fungistatic agents, an ETP antibody, pro-biotics, adsorbents, and introduction of non-glio-toxigenic species.

In certain embodiments, a provided composition is formulated for administration to a patient in need of such composition. In some embodiments, a provided composition is formulated for oral administration to a patient.

The term "patient" or "subject" as used herein, means an animal, such as a mammal, such as a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitory active metabolite or residue thereof.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration. Provided compositions may be formulate such that a dosage of between 0.01-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for diagnosis or treatment of disease, disorders, or symptoms thereof in a subject.

In certain embodiments, the invention provides a method of treating a disorder (as described above) in a subject, comprising administering to the subject identified as in need thereof, a compound based on the invention. The identification of those patients who are in need of treatment for the disorders described above is well within the ability and knowledge of one skilled in the art. Certain of the methods for identification of patients which are at risk of developing the above disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a disorder by methods well known in the art (e.g., determining tumor size or screening for tumor markers where the cell proliferative disorder is cancer) and then administering a therapeutically effective amount of a compound of the invention, to the subject. After an appropriate period of time after the administration of the compound (e.g., 1 day, 1 week, 2 weeks, one month, six months), the extent of the disorder is determined again. The modulation (e.g., decrease) of the extent or invasiveness of the disorder indicates efficacy of the treatment. The extent or invasiveness of the disorder may be determined periodically throughout treatment. For example, the extent or invasiveness of the disorder may be checked every few hours, days or weeks to assess the further efficacy of the treatment. A decrease in extent or invasiveness of the disorder indicates that the treatment is efficacious. The method described may be used to screen or select patients that may benefit from treatment with a compound of the invention.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

Compounds or compositions described herein may be administered using any amount and any route of administration effective for treating or lessening the severity of cancer or other proliferative disorder. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Provided compounds can be administered alone or in combination with one or more other therapeutic compounds, possible combination therapy taking the form of fixed combinations or the administration of a provided compound and one or more other therapeutic compounds being staggered or given independently of one another, or the combined administration of fixed combinations and one or more other therapeutic compounds. Provided compounds can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Such additional agents may be administered separately from a composition containing a provided compound, as part of a multiple dosage regimen. Alternatively, those agents may be part of a single dosage form, mixed together with a provided compound in a single composition. If administered as part of a multiple dosage regimen, the two active agents may be submitted simultaneously, sequentially or within a period of time from one another normally within five hours from one another.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "combination," "combined," and related terms refers to the simultaneous or sequential administration of therapeutic agents in accordance with this invention. For example, a provided compound may be administered with another therapeutic agent simultaneously or sequentially in separate unit dosage forms or together in a single unit dosage form. Accordingly, an embodiment of the invention provides a single unit dosage form comprising a provided compound, an additional therapeutic agent, and a pharmaceutically acceptable carrier, adjuvant, or vehicle for use in the methods of the invention.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions should be formulated such that a dosage of between 0.01-100 mg/kg body weight/day of a provided compound can be administered.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Pathobiology of Disease Implicated by the (GGI) or (D/DSI)

Glutathione loss by the fungal toxin Gliotoxin, then Acetaminophen in the peri-vaccination period, results in Metal Intoxication and Oxidative Stress-causing Regressive Autism.

Toxicity of Acetaminophen (APAP): is the most widely used analgesic worldwide. It is the most common cause of accidental poisoning and liver failure and became commonly used in early 1980s due to concern aspirin was causing Reye's syndrome. Coincident with the new use of APAP was the rapid rise of Autism cases. Acetaminophen overdose occurs when conjugative pathways become saturated. APAP is then oxidatively metabolized by liver p450 to NAPQI which normally is conjugated with glutathione and renally excreted.

Acetaminophen Pathophysiology: when glutathione levels are reduced, NAPQI binds to lipid hepatocytes and vital proteins, causing Oxidative Stress, inflammation and hepatocellular Zone III necrosis. The treatment for APAP overdose is N-Acetylcysteine—NAC, a glutathione precursor, and may enhance sulfate conjugation of free APAP. N-AC is also anti-inflammatory, an antioxidant, and increases Nitric Oxide levels and local tissue oxygen tensions—pO2. N-AC is best given within 8 hours, decreasing mortality. A new IV version called Acetadote is now currently available with expected improved outcomes.

Oxidant Stress, Reactive Nitrogen Species and APAP Toxicity: APAP depletes Glutathione (GSH) and binds to cellular and mitochondrial proteins. This inhibits and stresses mitochondrial respiration, causing ATP depletion. When Vitamin E is present, ROS do not induce lipid peroxidation, but superoxide anion reacts with Nitric Oxide—NO—to form peroxynitrite, thus modifying cell molecules and worsening mitochondrial dysfunction and ATP depletion. This known liver model is likely worse in the brain due to the dependence of the brain on blood borne glutathione. Neuronal Cells in the brain are wholly dependent on circulating blood borne Glutathione. Hence if circulating blood glutathione levels drop to below a critical level the brain is "starved" of glutathione, ATP, Oxygen use and localized cellular death is seen, as in Cerebral Palsy, which is characterized by Periventricular Leukomalacia—PVL. CP-PVL may represent the early extreme of a continuum of neurological syndromes of which Regressive Autism occurs at 24 months in the peri-vaccination period for MMR—mumps-measles-rubella vaccine.

Glutathione and Analgesics: GSH is a vital antioxidant, as it detoxifies drugs and reactive Oxygen species—ROS, regulates gene expression and effects membrane transport and apoptosis. Homeostasis is critical as turnover of GSH is dynamic; the precursors are the amino acids cysteine, glutamic acid and glycine. Toxic APAP levels deplete GSH, where depleted Glutathione is seen in AIDS, alcoholics, atherosclerosis, dyslipidemia, renal disease, malnutrition, cirrhosis, hepatitis, Pregnancy Induced hypertension—PIH, Eclampsia, Pre-eclampsia, and Toxemia of pregnancy, HELLP Syndrome, Gestational Diabetes, Diabetes, Cerebral Palsy, Peri-Ventricular Leukomlacia, Neonatal Jaundice, Bronchopulmonary Dysplasia, Multiple Sclerosis—MS, Macular Degeneration, Alzheimers, Parkinsonism, Amyotrophic Lateral Sclerosis, Schizophrenia, Ionizing Radiation poisoning, and other diseases of humans.

APAP, Measles, Mumps, Rubella (MMR) Vaccine & Autism: Schultz (UCSD) et al. (Autism—May 2008) using an on-line case control study surveyed 83 Autism families and 80 controls. APAP after MMR was significantly associated with Autism at O.R=6.1 (less than 5 y.o.). With Autism Regression only the O.R. was 3.97 and with post-vaccination sequelae only the O.R. was 8.23. Ibuprofen showed no association. Therefore, APAP after MMR is associated with Autism.

APAP Induced Oxidative Stress: Protection is afforded by N-Acetylcysteine: APAP increased cell and mitochondrial glutathione disulfide (GSSG) and altered GSSG: GSH ratio suggesting an oxidative stress role. Autistic children have elevated oxidized/reduced GSH ratio where normal children have 100 to 1 ratio of Reduced GSH to Oxidized GSH, this ratio is reversed in Regressive Autism children. Treatment with N-Acetyl Cysteine—a glutathione precursor—enhanced cell glutathione and reduced cellular loss. APAP-Oxidative Stress precedes cellular injury and is involved in spread of cell injury.

Oxidative Stress, Mitochondria and Glutathione Protection: Mitochondria provide energy and are involved in cell death by apoptosis. Oxidative phosphorylation generates Reactive Oxygen Species—ROS—from the electron transport chain. Superoxide anion and hydrogen peroxide—$H_2O_2$—are produced by transition metals in aerobic respiration. GSH in mitochondria is the only defense to $H_2O_2$. Glutathione is required to move GSH from the cytosol to the mitochondria. Glutathione transport is stabilized by Selenium-Adenosyl Methionine (SAM). Hence treatment for Autism should involve administration of Selenium and Methionine.

SAM and NAC are Protective against APAP Hepatotoxicity: SAM and NAC were compared in the treatment of APAP toxicity. In one study SAM was more protective than NAC. The Cysteine/Glutamate exchange modulates Glutathione supply for neuroprotection against Oxidative Stress. Glutathione synthesis is limited by Cysteine. NAC, SAM and GSH treatment raise Erythrocyte GSH. E-GSH may be cheapest—quick screening test for Autism susceptibility as most Glutathione is located in RBCs. Testing for GSH in RBCs could involve special preparation, such as freeze-drying and fracturing to release the intracellular contents. Anemia of pregnancy may be due to lysis of erythrocytes-RBCs by gliotoxin from Candida and other species.

Sulfate Metabolism is Abnormal in Autistic Children: Sulfation is important in metabolism of neurotransmitters and digestive hormones. Children with Autism had low APAP/sulfate glucuronide level—suggesting decreased sulfation capacity in the liver. This is associated with increased urinary sulfite and sulfate excretion. Sulfate metabolism defects in Autistic children are likely acquired due to fungal infestation and resultant mycotoxin production.

Glutathione Metabolism in CSF and the Blood Brain Barrier: Glutathione in the Choroid Plexus is metabolized like urine in the tubule in kidneys. CSF GSH can be modified by drugs that do not affect brain GSH. GSH mono-ethyl ester can be transported into CSF posing a possible potential treatment. Gamma-Glutamyl transpeptidase, which is high in the choroid plexus, is the only enzyme able to cleave the gamma-glutamyl bond of glutathione. Brain mitochondrion is more susceptible to GSH loss and Oxidative Stress than liver. H2O2, if not reduced, can lead to lipid hydroperoxides, damaging the mitochondrial membranes and their function. Autistic children show loss of Purkinje Cells and Increased Brain Volume.

Glutathione Redox State Regulates Mitochondrial Reactive Oxygen: Impaired Glutathione stores in Brain further increase mitochondrial ROS causing a cascade of further damage. To function as an antioxidant, Glutathione must be in the reduced form—to act as an electron donor. Normally there are 100 reduced GSH molecules vs. oxidized. Autistic patients have mostly oxidized GSH.

Glutathione Loss, Oxidative Stress and Metabolic Errors in Autism: Autistic children have Immune, Digestive, and Metabolic Abnormalities, i.e. low plasma inorganic sulfate and sulfur oxidation deficiencies. Irritable Bowel Disease (IBD) patients have low GSH—this deficiency may be a target for intervention. Many Autistic children have GI abnormalities and have bowel yeast/fungal issues such as GI Candidiasis producing ETP like toxins, such as Gliotoxin. Intrinsic defects in Immunity are seen in GI positive Autistic Syndrome Disorder (ASD) Children. Gliotoxin has been shown to kill CD4 cells, and in fact Autistic children have decreased CD4 cell counts and generalized immune suppression as seen in AIDS.

Oxidative Stress in Autism: This work has been done by A. & V. Chauhan who found Lipid Peroxidation markers are elevated in Autism. Transferrin (Iron binding) and Ceruloplasmin (Copper binding) levels are decreased, leading to altered Fe and Cu metabolism with sequelae. Antioxidant-Serum proteins are decreased, i.e. albumin, total protein which is seen also in Eclampsia, HELP Syndrome, Cancers, AIDS and others. Other enzymes altered include superoxide dismutase (SOD), glutathione peroxidase, catalase, homocysteine, methionine, farnesytransferase, causing inflammation, excitotoxicity, mitochondrial and generalized immune dysfunction. Alkaline phosphatase is elevated in many of these syndromes including Cerebral Palsy—CP, and alkaline phosphatase has been shown to be elevated after administration of Gliotoxin to camels.

GSH Determines Sensitivity toward Mercury-Hg-Induced Oxidative Stress: Cortical and Cerebellar Areas exhibit differential sensitivity to Mercury-induced ROS. Methylmercury (MeHg) is highly neurotoxic. GSH protects against MeHg neurotoxicity in neurons and astrocytes. Depletion of GSH increases MeHg toxicity and stress. GSH precursors—NAC & SAM—are neuroprotective. Acetaminophen—APAP, Gliotoxin and Mercury-Hg—are synergistic in Autism.

Thimerosol & Impaired Mitochondrial Oxidation/Reduction Activity: Ethyl-mercurithiosalicylic acid is an Ethyl-Hg releasing compound and has been in use 70 plus years. Thimerosol is 50% Mercury and thimerosol neurological damage is similar to that seen in Autism. TM is a preservative used in multi-dose vaccines. TM was removed from most vaccines in 2002 but the Autism epidemic continues unabated. Many vaccines still contain metals, such as vaccines given to newborns and many contain Aluminum as an adjuvant. Salicylates were linked to Mitochondrial Re-Dox impairment in Reye's syndrome as salicylates uncouple mitochondrial oxidative phosphorylation, as does Gliotoxin. Aspirin and Gliotoxin may act synergistically to cause Reye's syndrome. The role of aspirin in Reye's syndrome has been largely discredited. Once aspirin use was discouraged, the use of Acetaminophen soared and the Autism Epidemic began.

*Candida* and *Aspergillus* species yeasts produce Gliotoxin. Gliotoxin is immunosuppressive by killing CD4 cells, possibly causing AIDS and disrupts many enzyme systems. 32 of 50 of *Candida* tested produced an ETP-epipolythiodioxopioperazine-like compound. Gliotoxin, a hydrophobic molecule, was found in many cancer patients at MD Anderson in amounts far in excess of that required to cause pathology. 93% of *Aspergillus fumigatus*, 75% of *A. niger* and 25% *A. terreus* produced Gliotoxin. *A. fumigatus* had the highest concentrations of GT. *Penicillium* and *Trichoderma* can also make Gliotoxin. Other ETP toxins produced by fungi include Sirodesmin, Hyalodendrin, Spoidesmin A, Chaetomin, Chaetocin, Verticillins, Leptosin, Emestrin, Scabrosin, Dithiosilvatin, Epicorazine, Aranotin, Emethallicin. The methods herein can utilize any ETP toxin or other toxigenic mycotoxin, including those specifically delineated herein.

Gliotoxin Toxicity and Mode of Action: The toxicity of ETPs is due to the presence of the disulphide bridge, which inactivates proteins via reaction with thiol groups, and generation of ROS by Redox cycling. Gliotoxin possibly reacts with disulphide cysteine bonds in insulin causing loss of function and diabetes. Gliotoxin suppresses T-Cell response, inhibits the antigen presenting response and led to a preferential death of monocytes and derived dendritic cells as seen in AIDS. Physiological effects of GT are way below levels of GT found in cancer patients. Gliotoxin is a dangerous molecule. Gliotoxin production by *A. Fumigatus* may be an immunoevasive mechanism, acting on T cells.

Gliotoxin Pathobiology: Gliotoxin inactivates muscle Creatine Kinase—CK—by a reversible formation of a Disulfide Bond. CK is coupled to the regeneration of ATP to ADP and the Mitochondrial Permeability Pore (MPP). The Gliotoxin disulphide bond reacts with accessible cysteine residues on proteins, enzymes, hormones and synaptic receptors. Thus, there is a synaptic role in Autism also. GT inhibits alcohol dehydrogenase, reverse transcriptase, farnesyltransferase, and alters transcription factor NF kappa B. GT may similarly inactivate insulin in Gestational Diabetes and alter Nitric Oxide signaling, causing pregnancy induced hypertension—PIH. Bioactivity may be restored when treated with reducing agents as the oxidized forms showed loss of function. GT production and growth of human pathogenic yeasts in general, is favored by sex-steroid metabolism, such as progesterone, as seen in pregnancy, and by estrogen and testosterone.

Gliotoxin-Glutathione Adducts Deplete Physiological GSH Stores: Mechanism of Action of GT is disulfide linkage with sulfur nucleophiles in a thiol-disulfide exchange mechanism. GT/GSH equilibrium depends on pH and GSH level. Depletion of GSH by GT has numerous pathophysiological consequences. There is a ReDox dependent mechanism for GSH dependent reversible uptake of GT in cells. GT uptake to cells is dependent on GSH, and a 1500 fold increase of reduced GT is found intracellularly, as opposed to outside the cell. Oxidation of intracellular GT effluxes GT, and the efflux of GT is also caused by low GSH from cellular apoptosis. The above allows for a minor Gliotoxin production, while causing a maximum intracellular concentration, yielding maximum killer efficacy against a competitive organism. Decreased intracellular Glutathione after apoptosis by GT releases more GT for further cell killing like a "PacMan", devouring cells and then moving on to the next cell.

Metallothionein—MT—is regulated by Oxidative Stress and Metal Ions: MTs are small cysteine-rich (30%) heavy metal binding proteins which protect against stress and regulate Zinc and metal levels. Cysteine residues bind and store metal ions, such as Zn, Cu, Cd and others, such as mercury. MT has antioxidant capabilities and MT deficient knockout mice are sensitive to APAP hepatotoxicity. APAP and Gliotoxin deplete Glutathione, essentially creating Metallothionein deficient Autistic children.

Metallothionein and Zinc: MTs are involved in zinc metabolism: This control is linked to cellular Glutathione Status. Glutathione disulfide S-thiolation causes MT clusters to collapse and release Zinc. Zinc is released by oxidants, and antioxidants preserve this binding. A GSH/GSH disulfide redox coupling mechanism and selenium effect zinc delivery. Oxidation-Reduction state is critical to the direction of zinc transfer and distribution. MTs regulate mercury neurotoxicity, esp. MT III. MT perturbations are seen in Periventricular Leukomalacia—PVL, the hallmark of Cerebral Palsy—CP. This is associated with Premature Rupture of the Membranes—PROM—which is often treated with antibiotics, resulting in fungal overgrowth and production of mycotoxins, such as Gliotoxin. Treatment of patients with Cerebral Aspergillosis producing Gliotoxin have shown improvement in their condition by administration of intrathecal Glutathione via the cerebrospinal fluid—CSF.

Zinc Induced Neuronal Death is a possible pathology in Autism: Intracellular free zinc contributes to energy failure by loss of NAD+ and inhibition of glycolysis, prior to Mitochondrial Permeability Transition (MPT), inducing neuronal cell death. Zinc neuronal death is attenuated by oxaloacetate, dichloroacetate and niacinamide, which are possible treatments for Autism and CP. Zinc inhibits mitochondrial respiration at bc1 and alpha-ketoglutarate-dehydrogenase. Zinc is a novel intracellular second messenger with likely implications when disrupted.

Synaptic Cysteine Sulfhydryls are targets of Neurotoxicants: Sulfhydryl reactive metals (Hg, Cd, As, Pb) in the hair of Autistic children has been found lower than controls, leading to the conclusion these children had trouble excreting these metals. Impaired MT processing may be the etiology. These metals are likely bound to neurotransmission sites or other critical areas in Autistic children—causing the pathobiology.

Brain Neurotoxicity: Astrocytes are essential to provide GSH precursors to neurons. Thimerosol neurotoxicity is associated with GSH depletion. GSH provides defense against mercury toxicity. NAC & glutathione ethyl ester prevented cytotoxicity. GSH is poorly absorbed via GI tract so other routes must be chosen. These include transdermal, transnasal, IV, IM, oral based lipoceutical formulations, and others. There is a role for other neuroprotectants (SAM, B6, B12, thiamine, methionine etc.) Deficiency of thiamine can cause Werneke-Korsakoff Syndrome which leads to apoptosis—cell death—of neurons. Autism children have been shown to benefit from thiamine formulations.

The Etiology of Autism—Summary and Conclusions: Antibiotic Therapy changes GI flora favoring toxic yeasts. Antibiotics can also decrease the ability to detoxify metals by 90%, especially mercury. Gliotoxin is produced by the new GI flora by *Aspergillus* and *Candida*. Medicinal production in manufacturing of acetaminophen in facilities introduced *Aspergillus* spores into the end products as evidenced by formation of 2,4,6-tribromoanisole, which is formed by *Aspergillus*, most likely capable of Gliotoxin production. This resulted in a musty-moldy odor, which led to a massive product recall. Gliotoxin then adducts and depletes Glutathione to marginal levels. When GSH is less than 30% of normal or oxidized, APAP becomes toxic. Acetaminophen—at perivaccination period—is then associated with Critical Glutathione loss, especially in the brain by crossing the blood brain barrier—BBB. Gliotoxin and APAP both cause oxidative stress. GSH is needed for metal metabolism Thus, metallothionein—MT—and most metal metabolism and multiple enzyme pathways are affected, compounding the toxicology. This causes a "Perfect Storm" of Oxidative Stress, GSH Depletion, and Zinc and metal toxicity (Hg-Thimerosol), creating a condition of mitochondrial dysfunction in the brain—leading to hypoxia and Autism—similar to carbon monoxide—CO—poisoning. This also results in neurite pruning at a period of critical neurodevelopment which has long term consequences, as evidenced by axonal neuropathy and resultant Cerebral Palsy—CP. Multiple pathways of pathobiology possibly indicate multiple therapeutic modalities and preventive approaches, e.g. precursors, vitamins, avoidance of acetaminophen, etc.

Mycotoxins in general and aflatoxins in particular, are monitored and controlled in agricultural feed and foodstuffs to minimize their impact. Current Food and Drug Administration (FDA) regulations ban use of aflatoxin-contaminated corn and grain when aflatoxin levels exceed 20 parts per billion (ppb) and 0.5 ppb for milk. Similar regulations apply for other mycotoxins. Only as of 2009 has FDA had authority to regulate tobacco and as of 2012 mandated permissible levels of these toxins on all tobacco products. Presently there is no regulatory oversight to ensure that consumer products are adequately screened and treated for mycotoxins, such as aflatoxins, and gliotoxin. Furthermore, there is no publicly available information which reveals that adequate measures are being taken by industry to monitor, treat and remove these potent toxins and prevent fungal spore forming contamination of consumer products.

Modified Risk Tobacco Products—MRTPs—will benefit tobacco consumers, secondhand smokers, and the public at large. Specifically, regulation of mycotoxins in general and aflatoxin in particular will provide substantial public health benefits. Aflatoxin is a fungal toxin produced by *Aspergillus* and *Penicullium* fungi and is a complex aromatic heterocycle decomposing at 561 degrees Fahrenheit. Aflatoxin has been shown to survive in environmental tobacco smoke. *Aspergillus* is found worldwide as a storage fungus and production is favored by heat and humidity. Aflatoxin has been regulated by the FDA on all agricultural commodities such as milk, corn, grain, and peanuts since 1966, but, surprisingly, not on tobacco.

Hundreds of internal documents discovered in tobacco litigation along with others give us insight into work done in this area from the 1960s through today. More recently, p53 tumor suppressor gene research is evidence of aflatoxin contamination of tobacco. P53 is the guardian of the genome which instructs genetically-damaged cells to repair or die via apoptosis. P53 is the most common mutation in all cancers, and most laboratory cancer experiments use aflatoxin to mutate p53 as a positive control. The World Health Organization IARC (WHO-IARC) database analysis shows substantial mutations in human cancers consistent with an aflatoxin etiology. Most cancers show p53 mutations, especially lung, breast, and others. These may be due to aflatoxin, chemically known as a benzopyran, or to combustion of aflatoxin, leading to benzopyrene. Significantly, aflatoxin is 200 times more carcinogenic than benzopyrene, also a recognized tobacco carcinogen. Acting alone, aflatoxin or fungal toxigenic spores, which are semi-fire-resistant, may produce toxins in vivo, acting as infectious cancer foci. Focal Aspergillus spores, producing aflatoxin, mutate p53, while gliotoxin production would kill white blood CD4 cells, and generally be profoundly immunosuppressive, as seen in cancer. As such, aflatoxin and gliotoxin are biomarkers of toxin-producing fungal spores which may cause cancer in vivo. Additionally, they may colonize the human gastrointestinal—GI—tract where said toxins are produced and be taken up via the enterohepatic circulation, where they are ideally detoxified in the liver. However, if abnormalities in nutrients, minerals and antioxidant status are altered these toxins wreak havoc on their mammalian-human host. Aflatoxin is a carcinogen, teratogen, mutagen, inhibitor of protein synthesis, and is immunosuppressive. Aflatoxin and gliotoxin have been shown to increase HIV levels 500 percent, and both cause oxidative stress, an important emerging pathological state.

Therefore, aflatoxin and gliotoxin fungal-contaminated tobacco are likely contributing to the AIDS pandemic and numerous other human diseases by causing colonization of their host with mycotoxin producing yeasts and fungi. Other mycotoxins on tobacco are also potentially significant. In 1969, at North Carolina State, Welty performed intraperitoneal—IP—mouse injections of tobacco fungal extracts grown on baby food. A high percentage of toxic isolates causing death were found. After curing, *Aspergillus* was the most toxic with a lethality of 81 percent. *Alternaria* from brown spot disease has been shown to cause COPD in mice. Penicillic acid causes DNA breaks, possibly causing cancer.

*Aspergillus, Candida,* and *Penicillium* produce gliotoxin, depleting glutathione, which is implicated in Autism, HIV/AIDS, and cancer, via disruption of the crucial enzyme glutathione-S-transferase. Undoubtedly, there are many unappreciated mycotoxins associated with tobacco use with significant repercussions for MRTPs, the FDA, and the public health. A future regulatory framework through the FDA Center for Tobacco Products—CTP—would seek to regulate toxin levels on tobacco products in a manner similar to foodstuffs.

Aflatoxin or mycotoxin contaminations of tobacco are prime candidates for harm reduction strategy in implementation of MRTPs. Multiple technology solutions are available to limit the production of toxins on tobacco and consumer products. Monitoring of aflatoxin and mycotoxin contaminations from different curing practices will provide valuable data. Prevention, remediation, and terminal testing will result in a less harmful product, improving public health. Mycotoxin bioinformatics will yield insights into cancer etiologies, new therapies, diagnostic tests, and cures for many human diseases of current unknown etiology. If MRTPs are implemented, the individual consumer, second- and third hand smokers, will benefit through a less toxic product with less cancers, and other human diseases which are caused, promoted or enhanced by these mycotoxins. These include all the above mentioned diseases which are caused by glutathione depletion by gliotoxin and citrinin.

A number of alternative assaying techniques may be used to continuously or intermittently monitor levels of toxins. These assaying techniques include, but are not limited to, high-pressure liquid chromatography (HPLC), reversed-phase liquid chromatography and HPLC, RP-HPLC/UV detection, thin-layer chromatography, radioimmunoas say (RIA), antibody-linked RIA, ELISA, spectrophotometry, mass spectroscopy—MS, tandem MS, ES-MS, infrared spectroscopy, raman spectroscopy, lyophilized ligand-receptor complexes for assays and sensors, packed-flow cell fluorescence liquid chromatography (PFCFLC), antibody-linked immunoassay, adsorption chromatography, immuno-affinity chromatography, supercritical fluid extraction, bio-luminescence, chemical luminescence, NMR isotopic S35 labeled quantification, radioactive scintillation, chiro-optical spectroscopy, polarimetry, optical rotatory dispersion, circular dichroism, and circularly polarized luminescence, use of Ellman's reagent followed by UV-vis measurement, and others. Such testing methods are found in USPTO patent assigned to Lane—U.S. Pat. No. 6,058,940, as cited above.

With particular reference to gliotoxin, desired sample materials may be freeze fractured, osmotically, or otherwise removed from erythrocytes. This then allows for pH adjustment to effect optimum extraction, prior to reversed phase HPLC analysis, where retention times for gliotoxin are 17 minutes versus reduced gliotoxin at 15.8 minutes. This is adequate enough to enable accurate integration of the areas under the curve representing the quantity present. Using HPLC analysis with a UV spectrophotometer a 260 nM wavelength is desirable. The present invention also is directed to the entire class of ETP—epidithiapiperazin-ediones—toxins which have in common the unique di-annular disulphide bridge which is responsible for their toxicology. There are presently seventeen such known ETP mycotoxins, and it will be obvious to one skilled in the art that it is desirable to suspect these toxins may mimic gliotoxin in terms of pathobiology, but will not be detected if one is seeking only gliotoxin through an HPLC, MS, or other testing modality that is specific for gliotoxin only. Therefore, one further testing modality includes an antibody directed towards the active disulphide moiety of the ETP toxin. Said antibody, when coupled appropriately to a ligand, reagent radio-labeled target etc, will attach to said ETP toxin and allow for identification of same. See U.S. Pat. No. 4,772,551 to Hart et al., entitled "Method and Test Kit for Detecting a Trichothecene Using Novel Monoclonal Antibodies"; and U.S. Pat. No. 4,835,100 to Dixon et al. entitled "Method and Test Kit for Detecting an Aflatoxin $B_1$ and $G_1$ Using Novel Monoclonal Antibodies."

With respect to MS—mass spectroscopy—it will be apparent to one skilled in the art that Glutathione-Gliotoxin complexes with specific atomic mass units (AMUs) are within the realm of the invention, as are other Glutathione-ETP toxin mass spectroscopy atomic mass unit composites that might be found in test samples, which will vary widely as ETP toxins are of numerous AMUs.

In another embodiment of the invention, the skin or transparent fluids of the eye may be irradiated with optical radiation of a desired wavelength delivered and/or sensed, possibly through a fiber-optic device. In this, a continuous readout involves use of fiber-optic fibers or strands to carry and receive optical radiation used in the toxin identification process. The illumination apparatus may be located at a considerable distance from the point of toxin identification. Advantageously, use of fiber optics allows a plurality of wavelengths of light in close proximity to each other to be used for multiple toxin identification, and for a plurality of receiving fiber strands to be placed adjacent to each other, if necessary or desirable. The fiber optics may advantageously be mated to an electro-optical processing unit such that incident optical radiation is converted into an electrical analog or digital data stream, and the data is then transmitted electrically to a computer processing unit. In this, the test medium is illuminated at various specific frequencies and the reflected fluorescing radiation is transmitted back to a central computer. A program or algorithm designed to signal the presence of predetermined levels of toxins or other undesirable chemicals is preferably used to monitor levels of toxins in a living patient.

A further embodiment of the invention uses a cellular phone, I-phone, Android phone or other portable device to illuminate the skin, eye or other body part with a wavelength of light, and receives the reflected light signal back and sends the data via wired or wireless transmission to a computer which then interprets data and provides a readout indicative of toxin adduct status or content. Once the alert to excessive levels of toxin contamination is given, further treatment steps can be undertaken. The invention also includes administration of a chemical, compound, or pharmaceutical which will enhance identification of the desired toxin complex after a baseline level is established. See U.S. Pat. No. 3,763,374 to Tiffany et al. entitled "Dynamic Multistation Photometer-Fluorometer." Laser produced ultraviolet light is transmitted by fiber-optic cable (U.S. Pat. No. 3,992,631 to Harte, entitled "Fluorometric System, Method and Test Article") to illuminate, for example, aflatoxin-specific antibody-coated beads in the cuvetettes. The toxin-specific antibody-coated beads may be coated with antibodies specific to any toxin that is to be detected. The beads are contacted with effluent solvent, which is introduced in the cuvettes via inlets. The antibody bead-cuvettes preferably use fluorescent probes, which, when combined with antibodies for specific toxins, will fluoresce even if the toxin in question does not fluoresce well or at all. An accelerator reagent may be used, if desirable or necessary, and the cuvettes may be agitated, heated or otherwise treated to enhance assay sensitivity, as with addition of a cyclodextrin. Cepeda, A., et al., "Postcolumn Excitation of Aflatoxins Using Cyclodextrins in Liquid Chromatography for Food Analysis." Journal of Chromnatography, 1996; 721: 69-74.

Test cuvettes may be preloaded with toxin-specific antibody fluorescent probe complexes (TSAFPC) (Haugland, Richard P., Handbook of Fluorescent Probes and Research Chemicals, Sixth Ed. Molecular Probes, Inc., Eugene, Oreg., 1996) with pre-sealed needle-penetrable rubber stoppers, or test cuvettes may be loaded with toxin-specific antibody fluorescent probe complexes (TSAFPC) through inlet means just prior to testing a sample. An advantage of point of testing loading (POTL) of cuvettes is that the desired test may be chosen by a suitably programmed computer depending on the anticipated or suspected toxin and quantities present.

The toxin-specific antibody fluorescent probe complexes (TSAFPC) may be coated onto transparent microspheres of various sizes to obtain optimal fluorescence, thereby enhancing detection sensitivity. The TSAFPC-coated microspheres may be used in test cuvettes, as described above. Alternatively, the TSAFPC-coated microspheres may be affixed to a suitable substrate and used in the manner described above. Moreover, as another embodiment, the TSAFPC-coated microspheres may be introduced into a flowing solvent stream, captured by a restrictive or screen-type device, and illuminated with suitable optical radiation, and thereby, assayed. U.S. Pat. No. 4,181,853 to Abu-Shumays et al., entitled "Liquid Chromatography System with Packed Flow Cell for Improved Fluorescence Detection"; and U.S. Pat. No. 5,322,799 to Miller, Robert J. and James D. Ingle, entitled "Observation Cell and Mixing Chamber."

In addition to Gliotoxin, many other mycotoxins such as Aflatoxin, Citrinin, Sirodesmin, Hyalodendrin, Spoidesmin A, Chaetomin, Chaetocin, Verticillins, Leptosin, Emestrin, Scabrosin, Dithiosilvatin, Epicorazine, Aranotin, Emethallicin, Penicillic Acid, each which have their own specific excitation-emission frequencies or mass spectroscopy characteristics are thus subject to detection and potential treatment. Fungi known in particular are the species *Fusarium*, which produce zearealone, an estrogenic carcinogen. *Aspergillus ochraeus* can produce a mycotoxin known as ochratoxin, which is both a nephrotoxin and promoter of lung tumors.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

A blood sample is taken from an infant at 20 months who has had numerous bouts of otitis media with antibiotic treatment, and is at risk for GI yeast overgrowth. He may have oral thrush or Candidiasis. The sample is subjected to analysis for the qualitative and quantitative presence of glutathione (A), and the qualitative and quantitative presence of gliotoxin (B) using mass spectrometry. Upon determination of the levels of glutathione and gliotoxin, the ASI is calculated by dividing (A) by (B). An ASI of 10 or less indicates that the subject is at risk of autism and intervention is necessary. The subject is administered an agent that alters the ASI.

Example 2

A blood sample is taken from a pregnant parturient at sixteen weeks into her pregnancy. The sample is subjected to analysis for the qualitative and quantitative presence of glutathione (A), and the qualitative and quantitative presence of gliotoxin (B) using mass spectrometry. Upon determination of the levels of glutathione and gliotoxin, the G/GI is calculated by dividing (A) by (B). A G/GI of 10 or less indicates that the subject is at risk for Eclampsia/Pre-eclampsia/Pregnancy Induced Hypertension and intervention is necessary. The subject is administered an agent that alters the G/GI.

Example 3

A blood sample is taken from a premature neonate in the NICU, where the neonate is 26 weeks post-conception age and the mother has had PROM—Premature Rupture of Membranes—for two weeks. The neonate is at risk for Candidiasis due to administration of antibiotics to the mother for PROM. *Candida* producing gliotoxin depletes Glutathione and possibly subjects the neonate to PVL—peri-ventricular leukomalacia and CP—Cerebral Palsy. The sample is subjected to analysis for the qualitative and quantitative presence of glutathione (A), and the qualitative and quantitative presence of gliotoxin (B) using mass spectrometry. Upon determination of the levels of glutathione and gliotoxin, the G/GI is calculated by dividing (A) by (B). A G/GI of 10 or less indicates that the subject is at risk for PVL-CP and intervention is necessary. The subject is administered an agent that alters the G/GI.

Example 4

A blood sample is taken from a patient with AIDS. Gliotoxin has been shown to kill CD4 cells and return of immunocompetence is enhanced by adequate glutathione levels. The sample is subjected to analysis for the qualitative and quantitative presence of glutathione (A), and the qualitative and quantitative presence of gliotoxin (B) using mass spectrometry. Upon determination of the levels of glutathione and gliotoxin, the G/GI is calculated by dividing (A) by (B). A G/GI of 10 or less indicates that the subject is at risk for increased morbidity and mortality and intervention is necessary. The subject is administered an agent that alters the G/GI.

The following references describe diseases, disorders, and symptoms thereof that are implicated for treatment, monitoring and /or prevention using the compositions and methods herein:

| US Patents: | | |
|---|---|---|
| 4,126,701 | November 1978 | Taylor |
| 5,008,251 | April 1991 | Gruber |
| 5,225,407 | July 1993 | Oakley et al. |
| 5,527,825 | June 1996 | Karson et al. |
| 5,686,311 | November 1997 | Shaw |
| 5,837,729 | November 1998 | Bourinbaiar |
| 6,058,940 | May 2000 | Lane |
| 6,197,749 | March 2001 | Hamuro et al. |
| 6,270,953 | August 2001 | Malcus-Vocanson et al. |

-continued

| US Patents: | | |
|---|---|---|
| 6,362,226 | March 2002 | Phillips III et al. |
| 6,470,894 | October 2001 | Nersch et al. |
| 6,512,166 | January 2003 | Harman et al. |
| 6,790,825 | September 2004 | Beck et al. |
| 6,899,876 | May 2005 | Houston |
| 7,232,575 | June 2007 | Walsh et al. |
| 7,252,957 | August 2007 | Vojdani |
| 7,378,387 | May 2008 | Hamuro et al. |
| 7,452,681 | November 2008 | Amaral et al. |
| 7,534,450 | May 2009 | Walsh et al. |
| 7,604,948 | October 2009 | Amaral et al. |
| 7,749,509 | July 2010 | Cobb et al. |
| 7,803,531 | September 2010 | Fulton et al. |
| 7,939,066 | May 2011 | Puntenney et al. |
| 7,981,878 | July 2011 | Hubmann et al. |
| 8,170,803 | May 2012 | Kamath et al. |

1. Farrell MD, S. E., et. al.; Toxicity of Acetaminophen, Medscape Reference, Feb. 6, 2012, Asst. Prof. of Medicine, Harvard Med. School; Dept. of Emergency Medicine, Brigham and Women's Hospital, Boston, Mass.

2. Lauterburg B H; Analgesics and Glutathione, Am. J. Ther. 2002 May-June; 9(3):225-33, Department of Clinical Pharmacology, University of Bern, Bern, Switzerland.

3. The National Autistic Society; Acetaminophen use, measles-mumps-rubella vaccination, and autistic disorder, Schultz et al., Autism 2008 Vol. 12(3) 293-307.

4. M. L. Bajt, T. Knight, J. Lemasters, H. Jaeschke; Acetaminophen-Induced Oxidant Stress and Cell Injury in Cultured Mouse Hepatocytes: Protection by N-Acetyl Cysteine, M. Bajt, T. Knight, J. Lemasters, H. Jaeschke, Toxicological Sciences, 80, 343-349 (2004).

5. Oxidative stress: Role of mitochondria and protection by glutathione, BioFactors, 1872-8081, Issue Volume 8, Numbers 1-2/1998 Pages 7-11, J.C. Fernandez-Checal, C. Garcaia-Ruizl, A. Colell, A. Morales, M. Marai, M. Mirandal, E. Ardite, Instituto Investigaciones Biomedicas, Consejo Superior Investigaciones Cientaficas (CSIC), and Liver Unit, Department of Medicine, Hospital Clinic I Provincial, Barcelona, Spain.

6. An update of N-acetylcysteine treatment for acute acetaminophen toxicity in children. Curr. Opin. Pediatr. 2005 April; 17(2):239-45, L. Marzullo.

7. Comparison of S-Adenosyl-L-methionine and N-Acetylcysteine, Protective Effects on Acetaminophen Hepatic Toxicity, M. Terneus, K. Kiningham, A. Carpenter, S. Sullivan, M. Valentovic, J. of Pharmacology and Experimental Therapeutics, 2007 January; 320(1):99-107.

8. Abnormal Sulfate Metabolism in Autism, Horvath, K., Waring, R. H., Rabszlyn A., Blagg, S., Campbell, Z., Klovrza, L. V., Journal of Pediatric Gastroenterology and Nutrition, Volume 39, June 2004

9. Cystine/Glutamate Exchange Modulates Glutathione Supply for Neuroprotection from Oxidative Stress and Cell Proliferation, The Journal of Neuroscience, Oct. 11, 2006 26(41):10514-10523, A. Shih, H. Erb, X. Sun, S. Toda, P. W. Kalivas, T. Murphy. 10. Cysteine supplementation improves the erythrocyte glutathione synthesis rate in children with severe edematous malnutrition, A. Badaloo, M. Reid, T. Forrester, W. Heird and F. Jahoor, Am J Clin Nutrition, 2002 September; 76(3):646-52.

11. Glutathione metabolism at the blood-cerebrospinal fluid barrier, M. Anderson, M. Underwood, R. Bridges, A. Meister, Departments of Biochemistry and Neurobiology, Cornell University Medical College, NY, N.Y. 10021.

12. Evidence of Toxicity and Oxidative Stress and Neuronal Insult in Autism, J. Kern, A. Jones, Department of Psychiatry, University of Texas, Southwestern Medical Center at Dallas, Tex., USA, Journal of Toxicology and Environmental Health, Part B, 9:485-499, 2006.

13. Impairment of intestinal glutathione synthesis in patients with inflammatory bowel disease, B. Sido, V. Hack, A. Hochlehnert, H. Lipps, C. Herfarth, W. Droge, Gut 1998; 42:485-492.

14. Glutathione Depletion and Formation of Glutathione-Protein Mixed Disulfide Following Exposure of Brain Mitochondria to Oxidative Stress, V. Ravindranath and D. Reed, Biochemical and Biophysical Research Communications, Vol. 169, No. 3, Jun. 29, 1990, Pages 1075-1079.

15. The mycotoxins citrinin and gliotoxin differentially affect production of the pro-inflammatory cytokines tumour necrosis factor-alpha and interleukin-6, and the anti-inflammatory cytokine interleukin-10. 2005 June; 35(6):782-9. Clin Exp Allergy.

Johannessen L N, Nilsen A M, Løvik M. Department of Cancer Research and Molecular Medicine, Faculty of Medicine, Norwegian University of Science and Technology, Trondheim, Norway. Lene.Johannessen@medisin.ntnu.no 16. Oxidative stress in Autism, A. Chauhan, V. Chauhan, Pathophysiology, 13 (2006) 171-181.

17. The role of oxidant stress and reactive nitrogen species in acetaminophen hepatotoxicity. Toxicology Letters, 2003, Oct. 15; 144(3):279-88 Jaeschke H, Knight T R, Bajt M L.

18. Glutathione Redox State Regulates Mitochondrial Reactive Oxygen Production, The Journal of Biological Chemistry, Vol. 280, No. 27, Issue of July 8, pp. 25305-25312, 2005, D. Sen, T. Dalton, D. Nebert, H. Shertzer.

19. Role of glutathione in determining the differential sensitivity between the cortical and cerebellar regions towards mercury-induced oxidative stress, Toxicology, Volume 230, Issues 2-3, 12 Feb. 2007, Pages 164-177, P. Kaur, M. Aschner, T. Syversen.

20. The protective effects of glutathione against methyl mercury cytotoxicity, L. Kromidas, L. Trombetta, I. Siraj Jamall, Toxicology Letters, Volume 51, Issue 1, March 1990, Pages 67-80.

21. Glutathione modulation influences methyl mercury induced neurotoxicity in primary cell cultures of neurons and astrocytes, P. Kaur, M. Aschner, T. Syversen, Neurotoxicology 27 (2006) 492-500.

22. Mitochondrial dysfunction, impaired oxidative-reduction activity, degeneration, and death in human neuronal and fetal cells induced by low-level exposure to thimerosal and other metal compounds, D. A. Geier, P. G. King, M. R. Geier, Toxicological & Environmental Chemistry, Volume 91, Issue 4, June 2009, pages 735-749.

23. Dysregulated Innate Immune Responses in Young Children with Autism Spectrum Disorders: Their Relationship to Gastrointestinal Symptoms and Dietary Intervention, H. Jyonouchi, L. Geng, A. Ruby, B. Zimmerman-Bier, Neuropsychobiology 2005; 51:77-85.

24. Clinical isolates of yeast produce a Gliotoxin-like substance, D. Shah and B. Larsen, Mycopathologia, Vol. 116, Number 3, December 1991.

25. Frequency and Species Distribution of Gliotoxin-Producing *Aspergillus* Isolates Recovered from Patients at a Tertiary-Care Cancer Center, R. Lewis, N. Wiederhold, M. Lionakis, R. Prince, D. Kontoyiannis, Journal of Clinical Microbiology, December 2005, p. 6120-6126.

26. The epipolythiodioxopiperazine (ETP) class of fungal toxins: distribution, mode of action, functions and biosynthesis, D. Gardiner, P. Waring, B. Howlett, Microbiology (2005), 151, 1021-1032.

27. *Aspergillus fumigatus* suppresses the human cellular immune response via gliotoxin-mediated apoptosis of monocytes, M. Stanzani, E. Orciuolo, R. Lewis, D. Kontoyiannis, S. Martins, L. St. John, K. V. Komanduri, Blood, 2005; 105:2258-2265.

28. Effect of Gliotoxin on Human Polymorphonuclear Neutrophils, D. T. Shah, S. Jackman, J. Engle, and B. Larsen, Infectious Diseases in Obstetrics and Gynecology, 6:168-175 (1998).

29. Exacerbation of invasive aspergillosis by the immunosuppressive fungal metabolite, Gliotoxin, P. Sutton, P. Waring, A. Mullbacher, Immunology and Cell Biology (1996) 74, 318-322.

30. The Immunosupressive Fungal Metabolite Gliotoxin Specifically Inhibits Transcription Factor NF-kB, H. Pahl, B. Kraub, K. Schulze-Osthoff, T. Decker, E. Britta, Maureen Traenckner, M. Vogt, C. Myers, T. Parks, P. Waring, A. Mullbacher, A. Peter Czernilofsky, P. A. Baeuerle, J. Exp. Med., Volume 183, April 1996, 1829-1840.

31. The Isolation of Gliotoxin and Fumigacin From Culture Filtrates of *Aspergillus Fumigatus*, A. Menzel, O. Wintersteiner, J. C. Hoogerheide, The Journal of Biological Chemistry, p. 419.

32. Gliotoxin Causes Oxidative Damage to Plasmid and Cellular DNA, R. Eichner, P. Waring, A. Geue, A. Braithwaite, A. Mullbacher, The Journal of Biological Chemistry, Vol 263, No. 8, March 15, pp. 3772-3777, 1988.

33. Gliotoxins disrupt alanine metabolism and glutathione production in C6 glioma cells: a 13C NMR spectroscopic study, L. Brennan, C. Hewage, J. Malthouse, J. McBean, Neurochemistry International, 45 (2004) 1155-1165.

34. Immunosupression in vitro by a metabolite of a human pathogenic fungus. A. Mullbacher, R. D. Eichner, Proc. National Academy Science, USA, Vol. 81, pp. 3835-3837, June 1984.

35. Gliotoxin production by clinical and environmental *Aspergillus fumigatus* strains, C. Kupfahl, International Journal of Medical Microbiology, Volume 298, Issues 3-4, 1 Apr. 2008, Pages 319-327.

36. Detection of Gliotoxin in Experimental and Human Aspergillosis, R. Lewis, N. Wiederhold, J Han, K. Komanduri, D. Kontoyiannis, and R. Prince, Infection and Immunity, Jan. 2005, p. 635-637, Vol. 73, No. 1.

37. Gliotoxin inactivates alcohol dehydrogenase by either covalent modification or free radical damage mediated by redox cycling. Biochem Pharmacology 1995 May 11; 49(9): 1195-201.

Waring P, Sjaarda A, Lin Q H. John Curtin School of Medical Research, Australian National University, Canberra City.

38. Fungal Metabolite Gliotoxin Inhibits Assembly of the Human Respiratory Burst NADPH Oxidase, S. Tsunawaki, L. Yoshida, S. Nishida, T. Kobayashi, T. Shimoyama, Infection and Immunity, June 2004, p. 3373-3382.

39. Inactivation of Rabbit Muscle Creatine Kinase by Reversible Formation of an Internal Disulfide Bond Induced by the Fungal Toxin Gliotoxin, A. Hume, C. Chai, P. Waring, The Journal of Biological Chemistry, Vol. 275, No. 33, Issue of August 18, pp. 25202-25206, 2000.

40. Evidence for Gliotoxin-Glutathione Conjugate Adducts, P. Bernardo, C. Chai, G. Deeble, X. Ming Liu, P. Waring, Bioorganic & Medicinal Chemistry Letters, 11 (2001) 483-485.

41. A Novel Redox Mechanism for the Glutathione-dependent Reversible Uptake of a Fungal Toxin in Cells, P. Bernardo, N. Brasch, C. Cha, P. Waring, The Journal of Biological Chemistry, Vol. 278, No. 47, Issue of November 21, pp. 44549-46555, 2003.

42. Glutathione intensifies gliotoxin-induced cytotoxicity in human neuroblastoma SH-SY5Y cells, V. Axelsson, K. Pikkarainen and A. Forsby, Cell Biology and Toxicology, 2006; 22; 127-136.

43. Mechanism of Action of Gliotoxin: Elimination of Activity by Sulfhydryl Compounds, P. W. Trown, J. A. Bilello, Antimicrobial Agents and Chemotherapy, Oct. 1972, p. 261-266. Vol. 2, No. 4.

44. Anti-metallothionein IgG and levels of metallothionein in autistic children with GI disease. Russo A., Drug Health Patient Safety 2009; 1:1-8, Mount Saint Mary's University, Emmitsburg, Md., USA.

45. Metallothionein-I/II Knockout Mice are Sensitive to Acetaminophen-Induced Hepatotoxicity, J. Liu, Y. Liu, D. Hartley, C. Klaassen, S. Shehin-Johnson, A. Lucas, S. Cohen, The Journal of Pharmacology and Experimental Therapeutics, Vol. 289, No. 4, 289: 580-586, 1999.

46. Regulation of Metallothionein Gene Expression by Oxidative Stress and Metal Ions, G. Andrews, Biochemical Pharmacology, Vol. 59, pp. 95-104, 2000.

47. Oxidative metal release from metallothionein via zinc-thiol/disulfide interchange, W. Maret, Proc. Natl. Acad. Sci. USA, Vol. 91, pp. 237-241, January 1994.

48. The Function of Zinc Metallothionein: A Link between Cellular Zinc and Re-dox State, W. Maret, The Journal of Nutrition, p. 1455.

49. Control of zinc transfer between thionein, metallothionein, and zinc proteins, C. Jacob, W. Maret, B. Vallee, PNAS.

50. Metallothioneins: Mercury Species-Specific Induction and Their Potential Role in Attenuating Neurotoxicity, M. Aschner, T. Syversen, D. O. Souza, J. Rocha.

51. Phenotypic variation in xenophobic metabolism and adverse environmental response: focus on sulfur-dependent detoxification pathways, S. McFadden, Toxicology 111 (1996) 43-65.

52. Zinc-Induced Cortical Neuronal Death: Contribution of Energy Failure Attributable to Loss of NAD and Inhibition of Glycolysis, C. Sheline, M. Behrens, D. Choi, The Journal of Neuroscience, May 1, 2000, 20 (9): 3139-3146.

53. Zinc Irreversibly Damages Major Enzymes of Energy Production and Antioxidant Defense Prior to Mitochondrial Permeability Transition, I. Gazaryan, I. Krasinskaya, B. Kristal, A. Brown, Journal of Biological Chemistry, Vol. 282, Issue 33, 24373-24380, Aug. 17, 2007.

54. Zinc is a novel intracellular second messenger, S. Yamasaki, K. Sakata-Sogawa, A. Hasengawa, T. Suzuki, K. Kabu, E. Sato, T. Kurosaki, S. Yamashita, M. Tokunaga, K. Nishida, and T. Hirano, The Journal of Cell Biology, Vol. 177, No. 4, 637-645.

55. Sulfhydryl-Reactive Metals in Autism, J. Kern, B. Grannemann, M. Trivedi, Journal of Toxicology and Environmental Health, Part A, 70: 715-721, 2007.

56. Synaptic Cysteine Sulfhydryl Groups as Targets of Electrophilic Neurotoxicants, R. LoPachin, D. Barber, Toxicological Sciences, 94 (20), 240-255 (2006).

57. The Consequences of Methylmercury Exposure on Interactive Functions between Astrocytes and Neurons, J. Allen, G. Shanker, K. Tan, M. Aschner, Neurotoxicology 23 (2002) 755-759.

58. Thimerosol Neurotoxicity is Associated with Glutathione Depletion: Protection with Glutathione Precursors, S.

J. James, W. Slikker III, S. Melnyk, E. New, M. Pogribna, S. Jernigan, Neurotoxicology 26 (2005) 1-8.

59. Sequential Opening of Mitochondrial Ion Channels as a Function of Glutathione Re-dox Thiol Status, M. Aon, S. Cortassa, C. Mack, B. O'Rourke, The Journal of Biological Chemistry, Vol. 282, No. 30, pp. 21889-21900, Jul. 27, 2007.

60. Glutathione-coated Cadmium-Sulfide Crystallites in *Candida Glabrata*, Apr. 10, 1989, C. T. Dameron, B. R. Smith, and D. R. Winges, Departments of Medicine and Biochemistry, University of Utah Medical Center, Salt Lake City, Utah 84132

61. Gastrointestinal Candidiasis: Fact or Fiction? Timothy C. Birdsall, N D, Technical Director, Thorne Research, Inc.; Editor-in-Chief, Alternative Medicine Review.

62. Candida Glabrata, an Emerging Oral Opportunistic Pathogen, L. Li, S. Redding, and A. Dongari-Bagtzoglou, Department of Oral Health and Diagnostic Sciences, School of Dental Medicine, Univ. of Connecticut, Farmington, Conn. 06030-1710, USA; and Dept of General Dentistry, School of Dentistry, Univ. of Texas Health Science Center at San Antonio, San Antonio, Tex. 78229-3900, USA 63. Prophylactic systemic antifungal agents to prevent mortality and morbidity in very low birth weight infants. Clerihew L, Austin N, McGuire W, [Cochrane Database Syst Rev. 2004]

64. Pathogenic Yeasts *Cryptococcus neoformans* and *Candida albicans* Produce Immunomodulatory Prostaglandins, M. C. Noverr, S. M. Phare, G. B. Toews, M. J. Coffey and G. B. Huffnagle, Division of Pulmonary and Critical Care Medicine, Department of Internal Medicine, and Department of Microbiology and Immunology, University of Michigan Medical School, Ann Arbor, Mich. 48109-0642

65. International Peer Reviewed Publications on Gliotoxin, Dr Ambrose Furey, Safefood Biotoxin Research Network Co-ordinator, PROTEOBIO, Cork Institute of Technology, Bishopstown, Cork, IRELAND. E-mail: afurey@cit.ie 66. Mortality risk in selenium-deficient HIV-positive children. Campa A, Shor-Posner G, Indacochea F, Zhang G, Lai H, Asthana D, Scott G B, Baum M K., Center for Disease Prevention, Department of Psychiatry and Behavioral Sciences, University of Miami School of Medicine, Florida 33136, USA. J Acquir Immune Defic Syndr Hum Retrovirol 1999 Apr. 15; 20(5):508-13.

67. Immunosuppression in vitro by a metabolite of a human pathogenic fungus, A. Mullbacher, R. Eichner, Dept. of Microbiology and Immunology, John Curtin School of Medical Research, Australian National University, Canberra, A.C.T. 2601, Australia Proc. Natl. Acad. Sci. USA, Vol. 81, pp. 3835-3837, June 1984, Immunology 68. Effect of Administration of fungal toxin (Gliotoxin) in Clinical and Serobiochemical Parameters in Camels. M. S. Shathele, Dept of Microbiology, King Faisal University, International Journal of Pharmacology, 5 (6) 381-386, 2009.

69. The role of thioredoxin reductases in brain development, PLoS One, 2008 Mar. 19; 3(3):e1813, Soerensen J, Jakupoglu C, Beck H, Förster H, Schmidt J, Schmahl W, Schweizer U, Conrad M, Brielmeier M., Department of Comparative Medicine, Helmholtz Zentrum Munchen German Research Center for Environmental Health, Neuherberg, Germany.

70. The antioxidant N-acetylcysteine prevents accelerated atherosclerosis in uremic apolipoprotein E knockout mice. Ivanovski O, Szumilak D, Nguyen-Khoa T, Ruellan N, Phan O, Lacour B, Descamps-Latscha B, Drüeke T B, Massy Z A. INSERM Unit 507, Necker Hospital, Paris, France. ivanovski@necker.fr Kidney Int. 2005 June; 67(6):2288-94 Kidney Int. 2005 June; 67(6):2288-94

71. DNA fragmentation induced in macrophages by Gliotoxin does not require protein synthesis and is preceded by raised inositol triphosphate levels, Waring P., J Biol Chem. 1990 Aug. 25; 265(24):14476-80, Division of Cell Biology, John Curtin School of Medical Research, Australian National University, Canberra.

72. The p53 tumor suppressor network is a key responder to microenvironmental components of chronic inflammatory stress. Cancer Res. 2005, Nov 15; 65(22):10255-64. Staib F, Robles A I, Varticovski L, Wang X W, Zeeberg B R, Sirotin M, Zhurkin V B, Hofseth L J, Hussain S P, Weinstein J N, Galle P R, Harris C C. Laboratories of Human Carcinogenesis, Center for Cancer Research, National Cancer Institute, NIH, Bethesda, Md. 20892-4255, USA.

73. *Aspergillus fumigatus* toxicity and gliotoxin levels in feedstuff for domestic animals and pets in Argentina, G. A. Pena, C. M. Pereyra, M. R. Armando, S. M. Chiacchiera, C. E. Magnol, J. L. Orlando, A. M. Dalcero, C. Rosa and L. R. Cavaglieri, Letters in Applied Microbiology 2010 January; 50(1):77-81.

74. U.S. Dept. of Health and Human Services, Interagency Autism Coordinating Committee, Full Committee Meeting, Tuesday, Nov. 10, 2009, Rockville, Md., Thomas Insel, IACC Chair, NIMH, Della Hann, PhD, IACC Executive Secretary, Office of Autism Research Coordination, NIMH, Susan Daniels, PhD, Office of Autism Research Coordination, NIMH, James F. Battey, M.D., PhD, National Institute on Deafness and Other Communication Disorders, Ellen W. Blackwell, M.S.W., Centers For Medicare and Medicaid Services, Chris Degraw, M.D., M.P.H., HRSA, Lee Grossman, Autism Society, www.nealgross.com 75. Study of Glutathione, Vitamin C and Cysteine in Children With Autism and Severe Behavior Problems, University of Louisville, January 2011, University of Louisville, January 2011, Kosair Children's Hospital Foundation, Cumberland Pharmaceuticals, US Clinical Trial Registry.

76. Infant Sleep after Immunization: Randomized Controlled Trial of Prophylactic Acetaminophen, Linda Franck, Caryl L. Gay, Mary Lynch and Kathryn A. Lee, Pediatrics 2011; 128; 1100;

77. What do we know about the role of Gliotoxin in the pathobiology of *Aspergillus fumigatus*? Kyung J. Kwon-Chung and Janyce A. Sugui, Molecular Microbiology Section, Laboratory of Clinical Infectious Diseases, National Institute of Allergy and Infectious Diseases, National Institutes of Health, Bethesda, Md., USA78. Med Mycol. 2009; 47 (Suppl.1): S97-103

78. *Aspergillus* mycotoxins and their effect on the host, Kamai, Watanabe, Medical Mycology, 2005 May; 43 Suppl 1:S95-9. Research Center for Pathogenic Fungi and Microbial Toxicoses, Chiba University, Japan. k.kamei@faculty.chiba-u.j 79. Safety and efficacy of oral DMSA therapy for children with autism spectrum disorders: Part A—Medical results Division of Basic Medical Sciences, Southwest College of Naturopathic Medicine, Tempe, Az., USA, Adams, Baral, Geis et al., Department of Pediatric Medicine, Southwest College of Naturopathic Medicine, Tempe, Az., USA Autism Research Institute, San Diego, Calif., USA, Center for Integrative Pediatric Medicine, Tucson, Az., USA Department of Mathematics, Whittier College, Whittier, Calif., USA, International Child Development Resource Center, Phoenix, Az., USA, Department of Pediatrics, Tulane University School of Medicine, New Orleans, La., USA, BMC Clinical Pharmacology, 2009, 1472-6904-9-16.

80. BREAKING UP WITH ALEC IS HARD TO DO FOR JOHNSON & JOHNSON, SARA JERVING, FRI, 27 Apr. 2012/TRUTH-OUT.ORG

81. *Candida Albicans* and its metabolite gliotoxin inhibit platelet function via interaction with thiols, Bertling A, Neimann S., Department of Anaesthesiology and Intensive Care, Experimental and Clinical Haemostasis, University of Muenster, Muenster, Germany. Thrombosis Haemost, 2010 August; 104(2):270-8. Epub 2010 Apr. 29.

82. Early Onset *Candida* Infection in the Neonate: Risks and Trends, Rosenberg M, Garb J, Fisher D, Baystate Medical Center Children's Hospital, Baystate Medical Center Department of Surgery, Tufts University School of Medicine, Springfield, USA, Focus on Fungal Infections, No. 14.

83. The Autism Epidemic and Disappearing Bees: A Common Denominator? Dr Brian Moench, Wednesday, 25 Apr. 2012/TRUTH-OUT.ORG 84. Neuropathologic Substrate of Cerebral Palsy, R. D. Folkerth MD, Journal of Child Neurology, Vol. 20, No. 12, December 2005 pp. 940-949.

85. Chorioamnionitis as a risk factor for Cerebral Palsy-a Meta-analysis. Wu, Colford, JAMA 2000; 248:1417-1424.

85. Perinatal infection, inflammatory response, white matter damage, and cognitive limitations in children born preterm, Dammann, Kuban, Levitton, Ment Retard Dev Disabil Res Rev 2002; 8; 46-50.

86. Maturation-dependent vulnerability of oligodendrocytes to oxidative stress-induced death caused by glutathione depletion. J. Neuroscience 1998; 18:6241-6253.

87. High expression of tumor necrosis factor-alpha and interleukin-6 in periventricular leukomalacia. Yoon, Romero, Kim, Am J Obstet Gynecol 1997; 177:406-411.

88. Oxidative Injury in the Cerebral Cortex and Subplate Neurons in Periventricular Leukomalacia, Folkerth, Trachtenberg, Haynes, J Neuropathol Exp Neurol., 2008 July; 67(7): 677-686.

89. Developmental Regulation of manganese superoxide dismutase in rat oligodendrocytes confers protection against glutathione depletion induced toxicity, Soc Neurosci Abstr, 2004: 141.14.

90. Recurrent postnatal infections are associated with progressive white matter injury in premature infants. Glass H C, Bonifacio S L, Chau V, Glidden D, Poskitt K, Barkovich A J, Ferriero D M, Miller S P. Pediatrics 2008 August; 122(2):299-305, Department of Neurology, University of California, San Francisco, USA.

91. Systemic *Candida* infection in extremely low birth weight infants: short term morbidity and long term neurodevelopmental outcome. 2000 June; 19(6):499-504, Pediatric Infectious Disease, Friedman S, Richardson S E, Jacobs S E, O'Brien K. Department of Pediatrics, The Hospital for Sick Children, Toronto, Ontario, Canada. smadar@bigfoot.com 92. [Maternofetal disseminated candidiasis and high-grade prematurity]. Archives Pediatrics, 1997 April; 4(4): 331-4 [Article in French] Baud O, Boithias C, Lacaze-Masmonteil T, Ville Y, Guibert M, Zupan V, Chabernaud J L, André P, Nordmann P, Frydman R, Dehan M. Service de pédiatrie et réanimation néonatales, hôpital Antoine-Béclère, Clamart, France.

93. Prophylactic oral antifungal agents to prevent systemic *Candida* infection in preterm infants. Cochrane Database Syst Rev 2004; (1): CD003478 Austin N C, Darlow B.

Neonatal Intensive Care Unit, Christchurch Women's Hospital, Christchurch, New Zealand, Private Bag 4711, Christchurch, New Zealand.

94. Is periventricular leukomalacia an axonopathy as well as an oligopathy? Pediatr Res., 2001 April; 49(4):453-7 Dammann O, Hagberg H, Leviton A., Neuroepidemiology Unit, Department of Neurology, Children's Hospital, Boston, Mass. 02115, U.S.A.

95. Obstetric antecedents of intraventricular hemorrhage and periventricular leukomalacia in the low-birth-weight neonate. AM J Obstret Gynecol 1997 February; 176(2):275-81. Verma U, Tejani N, Klein S, Reale M R, Beneck D, Figueroa R, Visintainer P., Department of Obstetrics and Gynecology, New York Medical College, Westchester County Medical Center, Valhalla 10595, USA.

96. Gliotoxin as putative virulence factor and immunotherapeutic target in a cell culture model of cerebral aspergillosis. Mol Immonol., 2011 September; 48(15-16):2122-9. Epub 2011 Jul. 30. Speth C, Kupfahl C, Pfaller K, Hagleitner M, Deutinger M, Würzner R, Mohsenipour I, Lass-Flörl C, Rambach G. Department of Hygiene, Microbiology and Social Medicine, Innsbruck Medical University, Innsbruck, Austria, cornelia.speth@i-med.ac.at 97. Mycotoxin-induced depletion of intracellular glutathione and altered cytokine production in the human alveolar epithelial cell line A549. Toxicol Letters, 2007 Jan. 30; 168(2):103-12. Epub 2006 Nov. 15 Johannessen L N, Nilsen A M, Løvik M. Lene.Johannessen@ntnu.no 98. Gliotoxin causes oxidative damage to plasmid and cellular DNA. J Biol Chem., 1988 Mar. 15; 263(8):3772-7. Eichner R D, Waring P, Geue A M, Braithwaite A W, Müllbacher, 99. Mechanism of action of gliotoxin: elimination of activity by sulfhydryl compounds. Antimicrob Agents Chemother., 1972 October; 2(4):261-6. Trown P W, Bilello J A.

100. Recurrent postnatal infections are associated with progressive white matter injury in premature infants. Pediatrics, 2008 August; 122(2):299-305. Glass H C, Bonifacio S L, Chau V, Glidden D, Poskitt K, Barkovich A J, Ferriero D M, Miller S P.

101. Gliotoxin effects on fungal growth: mechanisms and exploitation. Fungal Genet Biol., 2012 April; 49(4):302-12, Carberry S, Molloy E, Hammel S, O'Keeffe G, Jones G W, Kavanagh K, Doyle S.

102. Single-pot derivatisation strategy for enhanced gliotoxin detection by HPLC and MALDI-ToF mass spectrometry. Anal Bioanal Chem., 2011 November; 401(8):2519-29, Davis C, Gordon N, Murphy S, Singh I, Kavanagh K, Carberry S, Doyle S.

103. Effect of N-chlorotaurine on *Aspergillus*, with particular reference to destruction of secreted gliotoxin, J. Med. Microbiology, 2006 July; 55 (Pt 7):913-8. Reeves E P, Nagl M, O'Keeffe J, Kelly J, Kavanagh K., Medical Mycology Unit, National Institute for Cellular Biotechnology, Department of Biology, NUI Maynooth, Co. Kildare, Ireland. emer.reeves@nuim.ir.

104. Amphotericin B enhances the synthesis and release of the immunosuppressive agent gliotoxin from the pulmonary pathogen *Aspergillus fumigatus*. J. Med. Microbiology 2004 August; 53(Pt 8):719-25. Reeves E P, Murphy T, Daly P, Kavanagh K., 105. Detection of *Aspergillus fumigatus* mycotoxins: immunogen synthesis and immunoassay development, J. Micrbiol Methods; 2004 February; 56(2):221-30, Fox M, Gray G, Kavanagh K, Lewis C, Doyle S. National Institute for Cellular Biotechnology, Department of Biology, National University of Ireland Maynooth, Maynooth, Co. Kildare, Ireland.

106. Manipulation of host angioneogenesis: A critical link for understanding the pathogenesis of invasive mold infections? Virulence; 2010 May-June; 1(3):192-6, Kontoyiannis D., Department of Infectious Diseases, Infection Control and Employee Health, The University of Texas MD Anderson Cancer Center, Houston, Tex., USA. dkontoyi@mdanderson.org 107. *Aspergillus fumigatus* suppresses the human cellular immune response via gliotoxin-mediated apoptosis of monocytes, Blood: 2005 Mar. 15; 105(6):2258-65. Epub 2004 Nov. 16. Stanzani M, Orciuolo E, Lewis R, Kontoyiannis D P, Martins S L, St John L S, Komanduri K V., Transplant Immunology Section, Department of Blood and Marrow Transplantation, MD Anderson Cancer Center, SCRB 3.3019, Unit 900, 7455 Fannin St, Houston, Tex. 77030, USA.

108. Increased astrocytic expression of metallothioneins I+II in brainstem of adult rats treated with 6-aminonicotinamide, Brain Research: 1997 Nov. 7; 774 (1-2):256-9. Penkowa M, Hidalgo J, Moos T., Dept. of Medical Anatomy, The Panum Institute, Univ. of Copenhagen, Denmark.

109. Metallothionein prevents neurodegeneration and central nervous system cell death after treatment with gliotoxin 6-aminonicotinamide. J. Neuroscience Res: 2004 Jul. 1; 77(1):35-53. Penkowa M, Quintana A, Carrasco J, Giralt M, Molinero A, Hidalgo J.Department of Medical Anatomy, The Panum Institute, University of Copenhagen, Copenhagen, Denmark.

110. Anti-metallothionein IgG and levels of metallothionein in Autistic families, Russo A F, Swiss Medical Weekly 2008 Feb. 9; 138(5-6):70-7, Science Department, Mount Saint Mary's University, Emmitsburg, Md. 21727, USA. russo@msmary.edu 111. Gliotoxin contamination in and pre- and post-fermented corn, sorghum and wet brewer's grains silage in Sao Paulo and Rio de Janeiro State, Brazil, Keller L A, Keller K M, Monge M P, Pereyra C M, Alonso V A, Cavaglieri L R, Chiacchiera S M, Rosa C A, J. Appl. Microbiology, 2012 May; 112(5):865-73.

112. Trace elements and antioxidant enzymes associated with oxidative stress in the pre-eclamptic/eclamptic mothers during fetal circulation. Negi R, Pande D, Karki K, Kumar A, Khanna R S, Khanna H D. Clin Nutr. 2012 May 2.

113. Oxidative stress and antioxidant status in neonates born to pre-eclamptic mother. Howlader M Z, Parveen S, Tamanna S, Khan T A, Begum F. J Trop Pedatrics, 2009 December; 55(6):363-7.

114. Role of oxidative stress in the pathogenesis of preeclampsia, Siddiqui I A, Jaleel A, Tamimi W, Al Kadri H M. Arch Gynecol Obstet., Siddiqui I A 2010 November; 282(5):469-74.

115. Differential proteomic analysis of highly purified placental cytotrophoblasts in pre-eclampsia demonstrates a state of increased oxidative stress and reduced cytotrophoblast antioxidant defense. Johnstone E D, Sawicki G, Guilbert L, Winkler-Lowen B, Cadete V J, Morrish D W, Proteonomics, 2011 October; 11(20):4077-84.

116. Role of oxidative stress markers and antioxidants in the placenta of preeclamptic patients. Rani N, Dhingra R, Arya D S, Kalaivani M, Bhatla N, Kumar R. J Obstet Gynaecol Res, 2010 December; 36 (6):1189-94.

117. Oxidative stress and antioxidant status in patients with late-onset gestational diabetes mellitus. López-Tinoco C, Roca M, García-Valero A, Murri M, Tinahones F J, Segundo C, Bartha J L, Aguilar-Diosdado M., Acta Diabeto., 2011 Feb. 17.

118. The role of oxidative stress in the pathophysiology of gestational diabetes mellitus. Lappas M, Hiden U, Desoye G, Froehlich J, Hauguel-de Mouzon S, Jawerbaum A., Antioxid Redox Signal, 2011 Dec. 15; 15(12):3061-100.

119. Altered placental oxidative stress status in gestational diabetes mellitus. Coughlan M T, Vervaart P P, Permezel M, Georgiou H M, Rice G E., Placenta, 2004 January; 25(1):78-84.

120. Influence of maternal redox status on birth weight, Osorio J C, Cruz E, Milanés M, Ramírez Y, Sierra M, Cruz M, Sanfiel L., Reprod. Toxicol, 2011 January; 31(1):35-40.

121. The importance of antioxidant micronutrients in pregnancy, Mistry H D, Williams P J., Oxid Med Cell Devel. 2011 Sep. 13.

122. U.S. Dept. of Health and Human Services, Food and Drug Admin. (FDA), Scientific Evaluation of Modified Risk Tobacco Product Applications: A Public Workshop, Thursday Aug. 25, 2011, Silver Spring, Md.

123. Low whole blood glutathione levels in pregnancies complicated by preeclampsia or the hemolysis, elevated liver enzymes, low platelets syndrome-HELLP Syndrome, Obstetr Gynecol, 1998 December; 92(6):1012-5, Knapen M F, Mulder T P, Van Rooij I A, Peters W H, Steegers E A.

124. Erythrocyte glutathione balance and membrane stability during preeclampsia. Free Radic Biol Med., 1998 April; 24(6):1049-55, Spickett C M, Reglinski J, Smith W E, Wilson R, 1998 July-August; 56(4):427.

125. Plasma glutathione S-transferase alpha 1-1: a more sensitive marker for hepatocellular damage than serum alanine aminotransferase in hypertensive disorders of pregnancy. AM J Obstet Gynecol, 1998 January; 178(1 Pt 1):161-5, Knapen M F, Mulder T P, Bisseling J G, Penders R H, Peters W H, Steegers E A.

126. Reduced glutathione prevents nitric oxide-induced apoptosis in vascular smooth muscle cells. Biochim Biophys Acta., 1997 Nov. 27; 1359(2):143-52. Zhao Z, Francis C E, Welch G, Loscalzo J, Ravid K.

127. Glutathione-S-transferase A4-4 modulates oxidative stress in endothelium: possible role in human atherosclerosis, Atherosclerosis, 2004 April; 173(2):211-21, Yang Y, Yang Y, Trent M B, He N, Lick S D, Zimniak P, Awasthi Y C, Boor P J.

128. Antioxidant role of glutathione S-transferases: protection against oxidant toxicity and regulation of stress-mediated apoptosis, Antioxid Redox Signal, 2004 April; 6(2):289-300. 2004

129. Aflatoxin, Tobacco, Ammonia and the p53 Tumor-Suppressor Gene: Cancer's Missing Link? Med Gen Med, 1999 Aug. 30: Lane K S.

130. [MSRV retrovirus and gliotoxin protein: potential biological markers in multiple sclerosis?] Ann Biol Clin, 1998 July-August; 56(4):427-38 [Article in French] Perron H.

131. Development and validation of a novel RP-HPLC method for the analysis of reduced glutathione, J Chromatog Sci, Sutariya V, Wehrung D, Geldenhuys W. 2012 March; 50(3):271-6.

132. Simultaneous determination of cefdinir and cefixime in human plasma by RP-HPLC/UV detection method: Method development, optimization, validation, and its application to a pharmacokinetic study, J Chromatog B Analyt Technol Biomed Life Sci., 2011 Aug. 15; 879(24):2423-9. July 6, Khan A, Iqbal Z, Khan M I, Javed K, Khan A, Ahmad L, Shah Y, Nasir F.

133. Applications of chiroptical spectroscopy for the characterization of pharmaceutical compounds. J Pharm Biomed Anal 1998 Sep. 1; 17(6-7):933-40. Brittain H G 134. Hypothesis: Fungal toxins are involved in aspergillosis and AIDS, Aust J Exp Biol Med Sci, 1984 August; 62 (Pt 4): 479-84 Eichner R D, Müllbacher A.

135. Exposure to mycotoxins increases the allergic immune response in a murine asthma model. Am J Respir Crit Care Med, Schütze N, Lehmann I, Bönisch U, Simon J C, Polte T. 2010 Jun. 1; 181(11):1188-99.

136. Neurologic and neuropsychiatric syndrome features of mold and mycotoxin exposure, Toxicol Ind Health, Empting L D. 2009 October-November; 25 (9-10):577-81.

137. Glutathione levels in antigen-presenting cells modulate Th1 versus Th2 response patterns, J. D. Peterson, L. A. Herzenberg, K. Vasquez, and C. Waltenbaugh, PNAS Mar. 17, 1998 vol. 95 no. 6, 3071-3076.

138. Gliotoxin from *Aspergillus fumigatus* affects phagocytosis and the organization of the actin cytoskeleton by distinct signaling pathways in human neutrophils, Microbes Infect., 2007 January; 9(1):47-54, Coméra C, André K, Laffitte J, Collet X, Galtier P, Maridonneau-Parini I.

139. In situ mycotoxin production by *Candida albicans* in women with vaginitis, Gynecol Obstet Invest., 1995; 39(1): 67-9, Shah D T, Glover D D, Larsen B.

140. Disturbed Glutathione Metabolism and Decreased Antioxidant Levels in Human Immunodeficiency Virus-Infected Patients during Highly Active Antiretroviral Therapy—Potential Immunomodulatory Effects of Antioxidants, J Infect Dis. (2003) 188 (2): 232-238, P. A., F. Muüller, A. M. Svarda, T. Ueland, R. K. Berge, S. S. Frøland.

141. A Pilot Study of the Effect of Inhaled Buffered Reduced Glutathione on the Clinical Status of Patients With Cystic Fibrosis' CHEST, January 2005 vol. 127 no. 1 308-317, C. Bishop, MD, FCCP, V. M. Hudson, PhD, S. C. Hilton, PhD, C. Wilde, BS.

142. The Effects of Sulfur Amino Acid Intake on Immune Function in Humans J. Nutr, June 2006, Vol. 136, No. 6, Robert F. Grimble.

143. Acetaminophen and Asthma, *Thorax*, Editorial, Victoria W Persky, 2010; 65:99-100.

144. Mycotoxin-induced depletion of intracellular glutathione and altered cytokine production in the human alveolar epithelial cell line A549, Toxicol Letters, 2007 Jan. 30; 168(2):103-12. Johannessen L N, Nilsen A M, Løvik M.

145. Transformation ability of fungi isolated from cork and grape to produce 2,4,6-trichloroanisole from 2,4,6-trichlorophenol, Food Additives and Contaminants, L. Maggi, V. Mazzoleni, M. D. Fumi, M. R. Salinas.

146. Children's Tylenol Recall: FDA slams factory conditions, CNN Fortune Money, Parija Kavilanz, May 4, 2010.

147. Tylenol Recall Expands, Nauseating 'Moldy' Odor From Tylenol Arthritis Pain Caplets, WebMD Health News, D. J DeNoon, L. Chang, Dec. 29, 2009.

148. Oxidative stress and antioxidant status in neonatal hyperbilirubinemia, Saudi Med J., 2008 December; 29(12): 1743-8, Davutoglu M, Guler E, Olgar S, Kurutas E B, Karabiber H, Garipardic M, Ekerbicer H C.

149. Metalloporphyrins in the management of neonatal hyperbilirubinemia, Semin Fetal Neonatal Med., June 15 (3) 164-168, D. K. Stevenson and R. J. Wong.

150. Oxidant and antioxidant levels in preterm newborns with idiopathic hyperbilirubinaemia, J Paedtric Child Health, 2004 November; 40(11):633-7, Turgut M, Basaran O, Cekmen M, Karatas F, Kurt A, Aygun A D.

151. Red blood cell and plasma glutathione peroxidase activities and selenium concentration in patients with chronic kidney disease: a review, Acta Biochim Pol., 2006; 53(4):663-77. Zachara B A, Gromadzińska J, Wasowicz W, Zbróg Z.

152. Maturation of the antioxidant system and the effects on preterm birth. Semin Neonatal Fetal Med., 2010 August; 15(4):191-5, Davis J M, Auten R L.

153. Future applications of antioxidants in premature infants. Curr Opinion Ped, 2011 April; 23(2):161-6, Lee J W, Davis J M.

154. Antioxidants and neonatal lung disease, Eur J Pediatr., 994; 153(9 Suppl 2):536-41. Russell G A.

155. Jaundice in new born and erythrocyte and plasma antioxidant defence system, Indian J Exper Biol., 1995 April; 33(4):303-5, Majumder S, Sarkar U, Sengupta D.

156. Determinants of oxidant stress in extremely low birth weight premature infants, Free Radic Biol Med., 2010 Nov. 15; 49(9):1380-6, Chessex P, Watson C, Kaczala G W, Rouleau T, Lavoie M E, Friel J, Lavoie J C.

157. Lower erythrocyte glutathione peroxidase activity in bronchopulmonary dysplasia in the first week of neonatal life, Neonatology, 2008; 93(4):269-75, Fu R H, Chiu T H, Chiang M C, Lien R, Chou Y H, Chiang C C, Cho Y H, Yang P H.

158. Hepatic glutathione and nitric oxide are critical for hepatic insulin-sensitizing substance action, Am J Physiol Gastrointest Liver Physiol, 2003 April; 284(4):G588-94. Guarino M P, Afonso R A, Raimundo N, Raposo J F, Macedo M P.

159. Insulin resistance after hypertension induced by the nitric oxide synthesis inhibitor L-NMMA in rats, AJP—Endo Oct. 1, 1995 vol, A. D. Baron, J. S. Zhu, S. Marshall, O. Irsula, G. Brechtel, C. Keech.

160. Influence of reduced glutathione infusion on glucose metabolism in patients with non-insulin-dependent diabetes mellitus, Metabolism, 1998 August; 47(8):993-7, De Mattia G, Bravi M C, Laurenti O, Cassone-Faldetta M, Armiento A, Ferri C, Balsano F.

161. Reduction of oxidative stress by oral N-acetyl-L-cysteine treatment decreases plasma soluble vascular cell adhesion molecule-1 concentrations in non-obese, non-dyslipidaemic, normotensive, patients with non-insulin-dependent diabetes, Diabetologia, 1998 November; 41(11):1392-6, De Mattia G, Bravi M C, Laurenti O, Cassone-Faldetta M, Proietti A, De Luca O, Armiento A, Ferri C.

162. Glutathione in human plasma: decline in association with aging, age-related macular degeneration, and diabetes, Free Radic Biol Med, 1998 Mar. 15; 24(5):699-704, Samiec P S, Drews-Botsch C, Flagg E W, Kurtz J C, Sternberg P Jr, Reed R L, Jones D P.

163. Low glutathione reductase and peroxidase activity in age-related macular degeneration, Br J Opthalmol, 1994 October; 78(10):791-4, Cohen S M, Olin K L, Feuer W J, Hjelmeland L, Keen C L, Morse L S.

164. Nitric oxide and lipid peroxidation are increased and associated with decreased antioxidant enzyme activities in patients with age-related macular degeneration, Doc Opthalmol, 2003 March; 106(2):129-36, Evereklioglu C, Er H, Doganay S, Cekmen M, Turkoz Y, Otlu B, Ozerol E.

165. Lipid peroxidation and antioxidant enzyme activities in erythrocytes of type 2 diabetic patients, J Med Assoc Thai, 2010 June; 93(6):682-93 , Likidlilid A, Patchanans N, Peerapatdit T, Sriratanasathavorn C.

What is claimed is:

1. A method, comprising:
   (a) measuring the level of glutathione in its reduced or oxidized state, or total glutathione in a sample from a subject;
   (b) measuring the level of gliotoxin in a sample from the subject;
   (c) administering to the subject, having below normal glutathione and toxicologically significant gliotoxin levels in the sample from the subject, one or more of antioxidants, anti-fungal and or fungistatic compounds, N-acetyl-cysteine, glutathione, selenium-adenosyl methionine (SAM), N-chlorotaurine to increase a ratio of the level of glutathione to the level of gliotoxin in the subject.

2. The method of claim 1, further comprising monitoring the subject by periodically calculating the ratio of the level of glutathione to the level of gliotoxin, and communicating the ratio to a health care practitioner.

3. The method of claim 1, further comprising measuring the levels of glutathione and gliotoxin independently or concurrently using a method that is: optical radiation detection, high-pressure liquid chromatography (HPLC), reversed-phase liquid chromatography and HPLC, RP-HPLC/UV detection, thin-layer chromatography, radioimmunoas say (RIA), antibody-linked RIA, ELISA, spectro-photometry, mass spectroscopy—MS, tandem MS, ES-MS, infrared spectroscopy, raman spectroscopy, lyophilized ligand-receptor complexes for assays and sensors, packed-flow cell fluorescence liquid chromatography (PFCFLC), antibody-linked immunoassay, adsorption chromatography, immuno-affinity chromatography, supercritical fluid extraction, bio-luminescence, chemical luminescence, NMR, isotopic S35 labeled quantification, radioactive scintillation, chiro-optical spectroscopy, polarimetry, optical rotatory dispersion, circular dichroism, circularly polarized luminescence, the use of Ellman's Reagent followed by UV-vis measurement, or any combination thereof.

4. The method of claim 1, wherein the sample is any bodily fluid, tissue hair, stool, urine, cerebrospinal fluid—CSF, expired respiratory gas, or flatulence.

5. The method of claim 1, wherein the samples are erythrocytes.

6. The method of claim 2, wherein the communicating is performed via a portable communication device, scanner, electronic handheld device, cellular phone.

7. The method of claim 1, wherein the administering comprises administering to the subject one or more of N-acetyl-cysteine and glutathione by either intranasal or rectal administration.

8. The method of claim 1, wherein the glutathione level in the sample from the subject is less than about 30% of normal or oxidized.

9. The method of claim 1, wherein the gliotoxin level in the sample from the subject is more than about 20 nanograms/ml.

10. The method of claim 1, wherein the subject is being treated for autism, cerebral palsy, or Alzheimer's disease.

11. The method of claim 1, further comprising periodically monitoring the ratio of glutathione level to gliotoxin level in the subject when the level of glutathione in the sample is below normal.

12. A method, comprising:
(a) measuring the level of glutathione in a sample from a subject;
(b) measuring the level of gliotoxin in a sample from the subject;
(c) if the level of glutathione in the sample from the subject is below normal and the level of gliotoxin in the sample is toxicologically significant, treating the subject to increase a ratio of the level of glutathione to the level of gliotoxin in the subject,
wherein the treating comprises administering to the subject one or more of anti-oxidants, anti-fungal and or fungistatic compounds, N-acetyl-cysteine, glutathione, selenium-adenosyl methionine (SAM), N-chlorotaurine by either intranasal or rectal administration.

13. The method of claim 12, wherein the glutathione is in its reduced state.

14. The method of claim 12, wherein the glutathione is in its oxidized state.

15. The method of claim 12, wherein the glutathione is its reduced or oxidized state or total glutathione, which is the sum of the oxidized and reduced glutathione.

16. The method of claim 12, further comprising monitoring the subject by periodically calculating the ratio of the level of glutathione to the level of gliotoxin, and communicating, via a portable communication device, scanner, electronic handheld device, or cellular phone, the ratio to a health practitioner.

17. The method of claim 12, wherein the subject is being treated for autism, cerebral palsy or Alzheimer's disease.

18. The method of claim 12, further comprising periodically monitoring the ratio of glutathione level to gliotoxin level in the subject when the level of glutathione in the sample is below normal.

19. The method of claim 12, wherein the glutathione level in the sample from the subject is less than about 30% of normal or oxidized.

20. The method of claim 12, wherein the gliotoxin level in the sample from the subject is more than about 20 nanograms/ml.

* * * * *